(12) United States Patent
Yan et al.

(10) Patent No.: US 7,445,909 B2
(45) Date of Patent: Nov. 4, 2008

(54) METHOD FOR DETECTING REACTIVE METABOLITES USING A COMBINATION OF GLUTATHIONE AND A STABLE ISOTOPIC DERIVATIVE OF GLUTATHIONE AND MASS SPECTROSCOPY-BASED PATTERN RECOGNITION

(75) Inventors: Zhengyin Yan, Drescher, PA (US); Gary W. Caldwell, Blue Bell, PA (US)

(73) Assignee: Janssen Phamaceutica N.V., Beerse (BE)

( * ) Notice: Subject to any disclaimer, the term of this patent is extended or adjusted under 35 U.S.C. 154(b) by 154 days.

(21) Appl. No.: 11/158,873

(22) Filed: Jun. 22, 2005

(65) Prior Publication Data

US 2005/0287623 A1   Dec. 29, 2005

Related U.S. Application Data

(60) Provisional application No. 60/583,386, filed on Jun. 28, 2004.

(51) Int. Cl.
*C12Q 1/26* (2006.01)
(52) U.S. Cl. .......................... 435/25; 436/57
(58) Field of Classification Search ............. 435/25; 436/57
See application file for complete search history.

(56) References Cited

U.S. PATENT DOCUMENTS

| | | | |
|---|---|---|---|
| 6,197,575 B1 | 3/2001 | Griffith et al. | |
| 2002/0034729 A1 | 3/2002 | Avery et al. | |
| 2003/0180962 A1* | 9/2003 | Kaplan et al. | ............... 436/86 |
| 2005/0186651 A1 | 8/2005 | Gan et al. | |
| 2008/0081349 A1 | 4/2008 | Huebert et al. | |

FOREIGN PATENT DOCUMENTS

| | | |
|---|---|---|
| EP | 1150120 A2 * | 10/2001 |
| WO | WO 91/08762 A1 | 6/1991 |
| WO | WO 03/027682 A | 4/2003 |

OTHER PUBLICATIONS

VandenHeuvel W. Drug Metabolite Identification: Stable Isotope Methods. J Clinical Pharmacology 26(6)427-434, Jul./Aug. 1986.*
Samuel K. et al. Addressing the Metabolic Activation Potential of New Leads in Drug Discovery . . . J of Mass Spectrometry, vol. 38, pp. 211-221, Jan. 2003.*
International Search Report PCT/US2005/022121 dated Oct. 28, 2005.
Yan, Zhengyin et al: "Stable-isotope trapping and high-throughput screenings of reactive metabolites using the isotope MS signature." Analytical Chemistry Dec. 1, 2004, vol. 76, No. 23, pp. 6835-6847 XP002348111.
Pearson P G et al: "Screening strategy for the detection of derivatized glutathione conjugates by tandem mass spectrometry" Analytical Chemistry, American Chemical Society Columbus, US, vol. 62, No. 17, 1990, pp. 1827-1836 XP001203557 ISSN: 0003-2700.
Baillie T A et al: "Mass spectrometry in the analysis of glutathione conjugates" Biological Mass Spectrometry, Wiley and Sons, Chichester, GB, vol. 22, No. 6, 1993, pp. 319-325 XP001016370 ISSN: 1052-9306.
Yan et al, "Stable-Isotope Trapping and High-Throughput Screenings of Reactive Metabolites Using the Isotope MS Signature," Anal. Chem., 2004, pp. 6835-6847, vol. 76, American Chemical Society, published on the web.
Mutilb et al, "Application of stable isotope labeled glutathione and rapid scanning mass spectrometers in detecting and characterizing reactive metabolites," Rrapid Commun. Mass Spectrom, 2005, pp. 3482-3492, vol. 19, Rapid Communications in Mass Spectrometry, John Wiley & Sons, Ltd.
Mutlib et al, "Formation of Unusual Glutamate Conjugates of 1-[3-(Aminomethyl) Phenyl]-N-[3-Fluoro-2'-(Methylsulfonyl)-1[1,1'-Biphenyl]-4-YL]3-(Trifuloromethyl)-1H-Pyrazole-5-Carboxamide (DPC 423) and Its Analogs: The role of γ-Glutamyltranspeptidase in the Biotransformation of Benzylamines," Drug Metabolism and Disposition, 2001, pp. 1296-1306, vol. 29, No. 10, The American Society for Pharmacology and Experimental Therapeutics, USA.
Borman et al, "Nipping Bad Drugs in the Bud," C&EN On line, 2004, pp. 36-39.
Evans et al, "Drug-Protein Adducts: An Industry Perspective on Minimizing the Potential for Drug Bioactivation in Drug Discovery and Development," Chem Res. Toxicol., 2004, pp. 3-16, vol. 17, American Chemical Society.
Gan et al, "Dansyl Glutathione as a Trapping Agent for the Quantitative Estimation and Identification of Reactive Metabolites," Chem Res. Toxicol., 2005, pp. 896-903, vol. 18, American Chemical Society.
Adang et al, "The glutathione-binding site in glutathione S-transferases," Investigation of the cysteinyl, glycyl and γ-glutamyl domains, J Biochem, 1990, pp. 47-54, vol. 269, Great Britain.

* cited by examiner

*Primary Examiner*—Ralph Gitomer
(74) *Attorney, Agent, or Firm*—Yuriy Stercho

(57) ABSTRACT

The present invention is directed to a method for detecting reactive metabolites using a combination of glutathione and a stable isotopic derivative of glutathione and mass spectroscopy. More specifically, the method selectively detects reactive metabolites by eliminating false positives arising from non-reactive components including both unreactive metabolites and components of the reaction mixture.

11 Claims, 20 Drawing Sheets

METHOD FOR DETECTING REACTIVE METABOLITES USING A COMBINATION OF GLUTATHIONE AND A STABLE ISOTOPIC DERIVATIVE OF GLUTATHIONE AND MASS SPECTROSCOPY-BASED PATTERN RECOGNITION

CROSS REFERENCE

This application claims the benefit of U.S. Provisional Application 60/583,386, Jun. 28, 2004, which is incorporated by reference herein in its entirety.

FIELD OF THE INVENTION

The present invention is directed to a method for detecting reactive metabolites using isotope trapping and mass spectroscopy. More specifically, the method selectively detects reactive metabolites, eliminating false positives.

BACKGROUND OF THE INVENTION

One cause of patient morbidity and mortality, idiosyncratic drug toxicity remains a serious safety concern in both clinical drug development and after market launch. These idiosyncratic drug reactions can lead to restricted use and even withdrawal from the market, which consequently results in higher development cost for the pharmaceutical industry. For example, troglitazone, benoxaprofen and zomepirac were withdrawn from the market shortly after their release due to unacceptable toxicity profiles.

Idiosyncratic drug reactions are a rare event that usually shows in a high degree of individual susceptibility. In addition, these reactions are usually not dose-dependent. Currently, there are no animal models that can be used to evaluate such reactions that exclusively occur in humans. Therefore, idiosyncratic drug toxicities cannot be effectively evaluated in preclinical studies, and are often unnoticed in clinical trials.

At present, the mechanisms of idiosyncratic drug reactions are not well understood. There is a substantial amount of evidence to suggest that chemically reactive metabolites are involved in idiosyncratic toxicities, especially for the liver. All drugs associated with idiosyncratic toxicity form reactive metabolites via various metabolic pathways mediated predominately by cytochrome P450s (CYPs), as well as by other oxidative enzymes such as peroxidases, cyclooxygenases and myeloperoxidases. It is hypothesized that drugs associated with such toxicities first undergo metabolic activation to generate toxic reactive metabolites that covalently bind to cellular proteins. These covalently modified proteins are immunogenic and thus trigger an immune response, resulting in idiosyncratic drug reactions. An alternative hypothesis states that covalent modifications of cellular proteins by reactive metabolites impair signal transduction cascades and vital functions of cells, leading to severe consequences observed in the clinic. Thus there remains a need for methods for identifying reactive metabolites.

Avery, Michael, J. (EP 1,150,120, Oct. 31, 2001) disclosed a high-throughput screening method for identifying drug candidates producing reactive metabolites. The method comprises incubating a drug candidate with a microsomal drug metabolizing enzyme system in the presence of glutathione and detecting glutathione conjugates formed therefrom using tanden mass spectrometry.

This method, however, will identify reactive metabolites as well as non-reactive components (including both unreactive metabolites and components of the reaction mixture) formed as a result of common response in mass spectrometry detection, thus resulting in false positives.

Thus, there remains a need for a method for detecting reactive metabolites which does not yield false positives.

SUMMARY OF THE INVENTION

The invention is directed to a method for detecting reactive metabolites of a drug candidate comprising (a) incubating a drug candidate with a mixture comprising a non-labeled trapping agent, an isotopically-labeled trapping agent, and a drug metabolizing enzyme; and (b) detecting one or more isotopic doublets in a neutral loss mass spectrum of a product of step (a), wherein the doublet differs in mass by the difference in mass between the non-labeled trapping agent and the isotopically-labeled trapping agent.

The invention is further directed to a mixture comprising (a) covalently bonded complex of a reactive metabolite and non-labeled trapping agent and (b) covalently bonded complex of a reactive metabolite and isotopically-labeled trapping agent.

BRIEF DESCRIPTION OF THE FIGURES

FIG. 5A—4-Hydroxyestrone total ion chromatogram of neutral loss scanning of 129 Da.

FIG. 5B—4-Hydroxyestrone mass spectrum for the most abundant component from the total ion chromatograph (at 5.11 min).

FIG. 6A—3-Methylindole total ion chromatogram of neutral loss scanning of 129 Da.

FIG. 6B—3-Methylindole mass spectra for the most abundant component from the total ion chromatograph (at 4.63 min (top), at 4.95 min (bottom), respectively).

FIG. 7A—p-Cresol total ion chromatogram of neutral loss scanning of 129 Da.

FIG. 7B—p-Cresol mass spectrum for the most abundant component from the total ion chromatograph (at 3.96 min).

DETAILED DESCRIPTION OF THE INVENTION

Figure 1A:
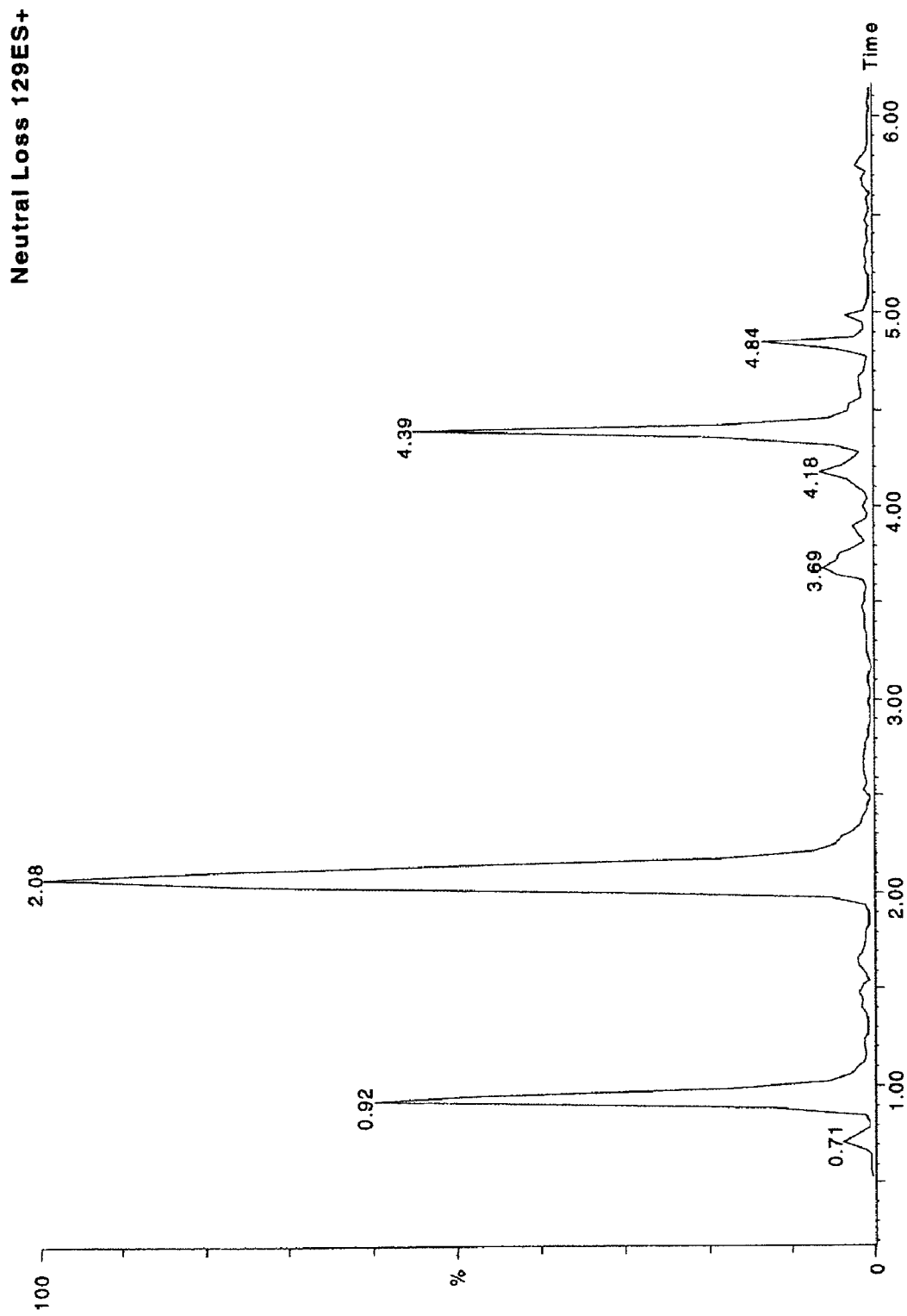
FIG. 1A—Acetaminophen total ion chromatogram of neutral loss scanning of 129 Da.

As used herein, unless otherwise noted, the terms "drug candidate" and "test compound" mean any chemical which is tested for the formation of reactive metabolites. Preferably, the drug candidate is a pharmaceutical agent or salt, ester or pro-drug thereof.

As used herein, unless otherwise noted, the term "trapping agent" means a methionine-containing peptide which reacts with a drug candidate or its metabolic intermediates to produce a peptide-drug adduct. Suitable examples include, but are not limited to, glutathione. Preferably, the trapping agent is glutathione (γ-glutamyl-cystein-glycin).

As used herein, unless otherwise noted, the term "isotopically-labeled trapping agent" means any trapping agent, for example glutathione, which is labeled with at least one isotope, for example, $^{13}C$, $^{15}N$, $^{18}O$, $^{2}H$, $^{3}H$, $^{34}S$, and the like. Suitable examples include, but are not limited to glutathione isotopically labeled with $^{13}C$ and/or $^{15}N$ at its cysteine group; glutathione isotopically labeled at both its cysteine and glycine groups; glutathione labeled at a single or multiple positions ranging from 1 to 17, preferably 1 to 5, more preferably 1 to 3; other stable isotope labeled tri-peptides that are substituted glycine with other amino acids, and the like. Preferably, the isotopically-labeled trapping agent is labeled with at least one isotope selected from the group consisting of $^{13}C$, $^{15}N$ and $^{2}H$. More preferably, the istopically-labelled trapping agent is glutathione labeled with two $^{13}C$ and one $^{15}N$ atoms (γ-glutamyl-cystein-glycin-$^{13}C2$-$^{15}N$).

Glutathione is a peptide of the following structure:

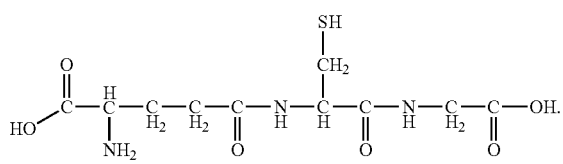

For ESI-MS/MS neutral loss scans of glutathione, the measured loss is, preferably, 129 Da, i.e., loss of the —C(O)—CH$_2$—CH$_2$—CH(NH$_2$)—CO$_2$H portion of the glutathione.

One skilled in the art will recognize that in the preferred isotopically-labeled glutathione, this portion (i.e. the portion lost in the neutral loss ESI-MS/MS) is not isotopically labeled.

Referring to the structure of glutathione shown above, other suitable trapping agents which may be used in the method of the invention include, but are not limited to, glutathione derivates wherein the —NH—CH$_2$—CO$_2$H portion is functionalized or derivatized with other amino acids, as would be readily known by one of ordinary skill in the art.

As used herein, unless otherwise noted "drug metabolite enzyme" means any enzyme or mixture thereof which can metabolize a drug candidate. Suitable examples include, but are not limited to a mixture of human liver microsomes, cytochrome P450, peroxidases, cyclooxygenases, myeioperoxidases, and the like. Preferably, the drug metabolite enzyme is a mixture of human liver microsomes, more preferably, cycotchrome P450.

As used herein, unless otherwise indicated, the term "adduct" means any covalently bonded complex of reactive metabolite and trapping agent.

Abbreviations used in the specification are as follows:

| | |
|---|---|
| APCI-MS/MS = | Atmospheric pressure chemical ionization tandem mass spectrometry |
| CYPs = | Cytochrome P450s |
| ESI-MS/MS = | Electrospray ionization tandem mass spectrometry |
| FIA-MS/MS = | Flow injection analysis tandem mass spectrometry |
| GSH = | γ-glutamyl-cystein-glycin |
| GSX = | γ-glutamyl-cystein-glycin-$^{13}$C2-$^{15}$N |
| HPLC = | High pressure liquid chromatography |
| MS = | mass spectroscopy |
| NAPDH = | β-nicotinamide adenine dinucleotide phosphate (reduced) |
| SPE = | Solid phase extraction |

The invention is directed to a method for detecting reactive metabolites using isotope trapping and mass spectrometry, wherein the method eliminates false positives. The invention further provides a highly sensitive method for detecting reactive metabolites at low levels. Additionally, the invention may be applied to the detection of reactive metabolites in a manual or in a fully automated manner using MS pattern recognition.

The invention is directed to a method for detecting of reactive metabolites of a drug candidate comprising (a) incubating a drug candidate with a mixture comprising a non-labeled trapping agent, an isotopically-labeled trapping agent, and a drug metabolizing enzyme; and (b) detecting one or more isotopic doublets in a neutral loss mass spectrum of a product of step (a), wherein the doublet differs in mass by the difference in mass between the non-labeled trapping agent and the isotopically-labeled trapping agent.

In an embodiment, the invention is directed to a method for detecting reactive metabolites of a drug candidate comprising (a) incubating a drug candidate with a mixture comprising a non-labeled trapping agent, an isotopically-labeled trapping agent, and a drug metabolizing enzyme;

(b) separating the products of step (a) and then measuring a neutral loss mass spectrum of each of said products; and (c) detecting one or more isotopic doublets in the neutral loss mass spectra, wherein the doublet differs in mass by the difference in mass between the non-labeled trapping agent and the isotopically labeled trapping agent.

In an embodiment of the invention, the non-labeled and isotopically-labeled trapping agents are glutathione (GSH, γ-glutamyl-cystein-glycin) and glutathione labeled with two $^{13}$C and one $^{15}$N atoms (GSX, γ-glutamyl-cystein-glycin-$^{13}$C2-$^{15}$N), respectively.

In an embodiment of the invention, the neutral loss mass spectrum is used to detect loss of 129 Da (corresponding to the loss of the —C(O)—CH$_2$—CH$_2$—CH(NH$_2$)—CO$_2$H portion of the non-labeled or isotopically-labeled glutathione).

In an embodiment of the invention, the doublet(s) are detected following APCI-MS/MS. ESI-MS/MS or FIA-MS/MS, preferably ESI-MS/MS or FIA-MS/MS, more preferably, FIA-MS/MS.

In an embodiment of the invention, the doublet in the neutral loss mass spectrum differs by a mass of between 1 and 10 mass units, preferably between 2 and 5 mass units, more preferably by 3 mass units.

In an embodiment of the invention, the drug metabolism enzyme is selected from the group consisting of a mixture of human liver microsomes, cytochrome P450s, peroxidases, cyclooxygenases and myeloperoxidases. Preferably, the drug metabolism enzyme is cytochrome P450.

In an embodiment, the method of the invention is applied to detecting reactive metabolites formed in cells, for example in hepatocytes. In another embodiment, the invention is applied to detecting reactive metabolites formed by reacting a drug candidate with any fraction of cells containing drug metabolism enzymes, for example, S9, recombinant enzymes or microsomal enzymes.

Preferably, the method of the invention is applied to predict the formation of reactive metabolites upon administration to a human.

The invention is further directed to a mixture comprising (a) covalently bonded complex of a reactive metabolite and non-labeled trapping agent and (b) covalently bonded complex of a reactive metabolite and isotopically-labeled trapping agent.

In an embodiment of the invention, the molar ratio of the covalently bonded complex of a reactive metabolite and non-labeled trapping agent and the covalently bonded complex of a reactive metabolite and isotopically-labeled trapping agent is about 1:1.

The invention is directed to a method for detecting reactive metabolites. More specifically, in the method of the invention, a drug candidate or test compound (Q) is reacted with a mixture comprising (a) non-labeled trapping agent, (b) isotopically-labeled trapping agent; wherein the non-labeled and isotopically-labeled trapping agents are chemically equivalent, for example, non-labeled glutathione (GSH) and isotopically-labeled glutathione (GSX) wherein the isotopically-labeled glutathione contains two $^{13}$C and one $^{15}$N atoms, and the like; preferably, at a molar ratio of non-labeled trapping agent to isotopically-labeled trapping agent of about 1:1 (to yield doublets in the mass spectrum which have about the same intensity); and (c) drug metabolizing enzyme such as, a mixture of human liver microsomes, cytochrome P450s (CYPs) (purified, recombinant, in microsomes, in hepatic cells, and the like), peroxidases, cyclooxygenases, myeloperoxidases, and the like; according to known methods, to yield a product mixture comprising non-reactive metabolites and adducts formed between said non-labeled and isotopically-labeled trapping agents and reactive metabolites (M). One skilled in the art will recognize that the non-reactive (stable) metabolites will not react with the trapping agent, but will remain in the mixture unaltered.

Preferably, the isotopically-labeled trapping agent is labeled with one or more isotopes which are selected to be stable. Suitable isotopes include, but are not limited to, $^{13}$C, $^{15}$N, $^{2}$H, $^{3}$H, $^{18}$O, $^{34}$S, and the like. Preferably, the isotopes are selected from the group consisting of $^{13}$C, $^{15}$N and $^{2}$H.

Preferably, the isotopically-labeled trapping agent differs in mass from the non-labeled trapping agent by between 1 and 10 mass units, more preferably between 2 and 5 mass units, most preferably 3 mass units.

The product mixture containing the non-reactive metabolites and the adducts formed between the trapping agents and reactive metabolites is preferably cleaned and concentrated according to known methods, for example by SPE or liquid-liquid extractions, to yield a product concentrate. The product concentrate is then dissolved in a solvent suitable for use in mass spectroscopy (i.e., suitable for injection into a mass spectrometer), for example, 5% acetonitrile in water.

Preferably, the product mixture is separated into its products or product components according to known methods, for example by liquid chromatography, HPLC, capillary electrophoresis, or other separation technique. A neutral loss mass spectrum is then measured for each product or product component. The neutral loss mass spectrum may be measured according to known methods, using any ionization source, for example by APCI-MS/MS, ESI-MS/MS, and the like, preferably by ESI-MS/MS. Alternatively, the separation and mass spectrum measurement may be completed in one step using a loop system such as, LC/MS, FIA-MS/MS, and the like, preferably FIA-MS/MS.

If reactive metabolites are present (as adducts with the non-labeled and isotopically-labeled trapping agent), the corresponding mass spectra will exhibit one or more doublets spaced by the difference in mass between the non-labeled and isotopically-labeled trapping agents. Thus for example, wherein the non-labeled trapping agent is glutathione and the isotopically-labeled trapping agent is glutathione labeled with two $^{13}$C and a single $^{15}$N, the doublet will be spaced by 3 Da.

One skilled in the art will recognize that the doublet(s) may be identified either by visual recognition or by using a computer software program which evaluates MS patterns.

In the process of the invention, false positives are readily eliminated since they do not exhibit a characteristic doublet in the measured neutral loss mass spectrum.

As an example, where the non-labeled trapping agent is glutathione and the isotopically-labeled trapping agent is glutathione labeled with two $^{13}$C and on $^{15}$N atoms, and the non-labeled and isotopically-labeled trapping agents are used at a molar ratio of 1:1, in collision-induced dissociation, both the non-labeled and isotopically-labeled adducts will undergo a neutral loss of pyroglutamate (129 Da). As a result, the MS spectra of adducts formed between a reactive metabolite and the non-labeled glutahtione and istopically-labeled glutathione will exhibit two isotopic molecular ions that differ in mass by 3 Da, and the isotopic doublet will show approximately equal intensities. A consistent mass difference of 3 Da and equal intensity of said doublet peaks would thereby provide a unique MS signature which would identify the reactive metabolite adduct.

Automation of the method of the invention may be accomplished, for example, by using computer-assisted MS pattern recognition. As an example, a logical diagram was devised to program a computer to perform automatic detection of reactive metabolites. More specifically, the pattern recognition process consisted of the following steps:

1. defining the error tolerance for the m/z value;
2. defining the error range of peak intensity ratio for a potential isotope doublet;
3. determining chromatographic peaks in the total ion chromatogram with a selected noise-to-signal setting;
4. detecting m/z values of major molecular ions of individual chromatographic peaks;
5. searching for doublets that differed in mass by 3 Da (or as otherwise appropriate based on the selected isotope types and number) using defined the error tolerance;
6. determining the intensity ratios of identified doublets; and
7. identifying GSH adducts.

In using this approach, the intensity ratio and the mass difference of the doublet(s) are the most determining parameters in pattern recognition. Error ranges of the intensity ratio are determined by the purity of non-labeled and isotopically-labeled trapping agent, while the error tolerance of m/z values is dependent on the performance of mass spectrometers.

The following Examples are set forth to aid in the understanding of the invention, and are not intended and should not be construed to limit in any way the invention set forth in the claims which follow thereafter.

EXAMPLE 1

Standard Procedures

A. Incubation & Stable Isotope Trapping:

All microsomal incubations described herein were performed at 37° C. in a water bath. The test compound (or drug candidate) was mixed with human microsomal proteins in 50 mM potassium phosphate buffer (pH 7.4) supplemented with GSH and GSX that were pre-mixed at an equal molar ratio of 1:1. Reaction mixtures were then warmed at 37° C. for 5 min. The reactions were initiated by the addition of a NADPH generating system to yield a final volume of 1000 µL. The final reaction mixtures contained 10 µM test compounds, 1 mg/mL microsomal proteins, 1 mM GSH and GSX, 1.3 mM NADP$^+$, 3.3 mM glucose-6-phosphate, 0.4 U/ml glucose-6-phosphate dehydrogenase, 3.3 mM magnesium chloride. After a 60 min incubation, the reactions were terminated by the addition of 150 µL of trichloroacetic acid (10%). The samples were centrifuged at 10,000 g for 15 min at 4° C. to pellet the precipitated protein, and the supernatants were subjected to solid-phase extractions. Alternatively, the reaction mixtures were subjected to liquid-liquid extractions to recover the metabolites from supernatants.

B. Mass Spectrometry:

MS analyses were performed on a Micromass (Manchester, UK) Quattro Micro triple quadrupole mass spectrometer. The ESI ion source was operated in the positive ion mode, and experimental parameters were set as follows: capillary voltage 3.2 kV, source temperature 120° C., desolvation temperature 300° C., sample cone voltage 26 V. Mass spectra collected in the neutral loss scanning mode were obtained by scanning over the range m/z 400-800 in 2.0 sec.

C. LC-MS/MS Analyses:

For complete profiling of reactive metabolites, samples were first subjected to chromatographic separations with an Agilent 1100 HPLC system with an auto-sampler (Agilent Technologies, Palo Alto, Calif.), and eluents were introduced to the Quattro Micro triple quadrupole mass spectrometer operated in the neutral loss scanning mode. An Agilent Zorbax SB C18 column (2.1×50 mm) was used for the chromatographic separation. The starting mobile phase consisted of 95% water (0.5% acetic acid), and the metabolites were eluted using a single gradient of 95% water to 95% acetonitrile over 7 min at a flow rate of 0.3 mumin. At 7 min, the column was flushed with 95% acetonitrile for 2 min before re-equilibration at initial conditions. LC-MS/MS analyses were carried out on 10-µL aliquots of cleaned samples. Data were processed using the Masslynx version 4.0 software from Micromass. After a positive peak was detected, MS/MS spectra were subsequently obtained to further confirm the structure of the glutathione conjugate. To acquire CID spectra, the mass spectrometer was operated in the multiple reaction monitoring (MRM) mode.

D. Flow Injection-MS/MS analyses:

For rapid screening of reactive metabolites (as described in Example 11), cleaned samples were directly injected to the mass spectrometer that was operated in the neutral scanning mode. An Agilent 1100 autosampler was used as a flow injection device to introduce cleaned samples into the mass spectrometer. The mobile phase consisted of 50% water (0.5% acetic acid) and 50% acetonitrile. MS data acquisition was completed in 0.5 min. After a glutathione conjugate was detected, CID MS/MS spectrum was subsequently acquired to determine the structure of the glutathione conjugate.

EXAMPLE 2

Acetaminophen

Acetaminophen's metabolites are well characterized in the art. More particularly, acetaminophen is known to form the reactive metabolite N-acetyl-p-benzoquinone imine (NAPQI) via oxidation reactions mediated by CYPs as shown in Scheme 1.

Scheme 1

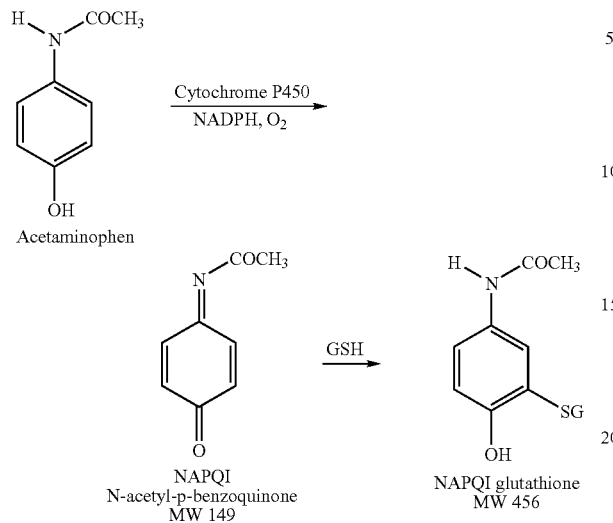

Acetaminophen
NAPQI
N-acetyl-p-benzoquinone
MW 149
NAPQI glutathione
MW 456

In the in-vitro incubation, NAPQI, the known reactive metabolite, was trapped to form two isotopic glutathione adducts (NAPQI-SG, 456 Da; NAPQI-SGx, 459 Da).

Figure 1B:
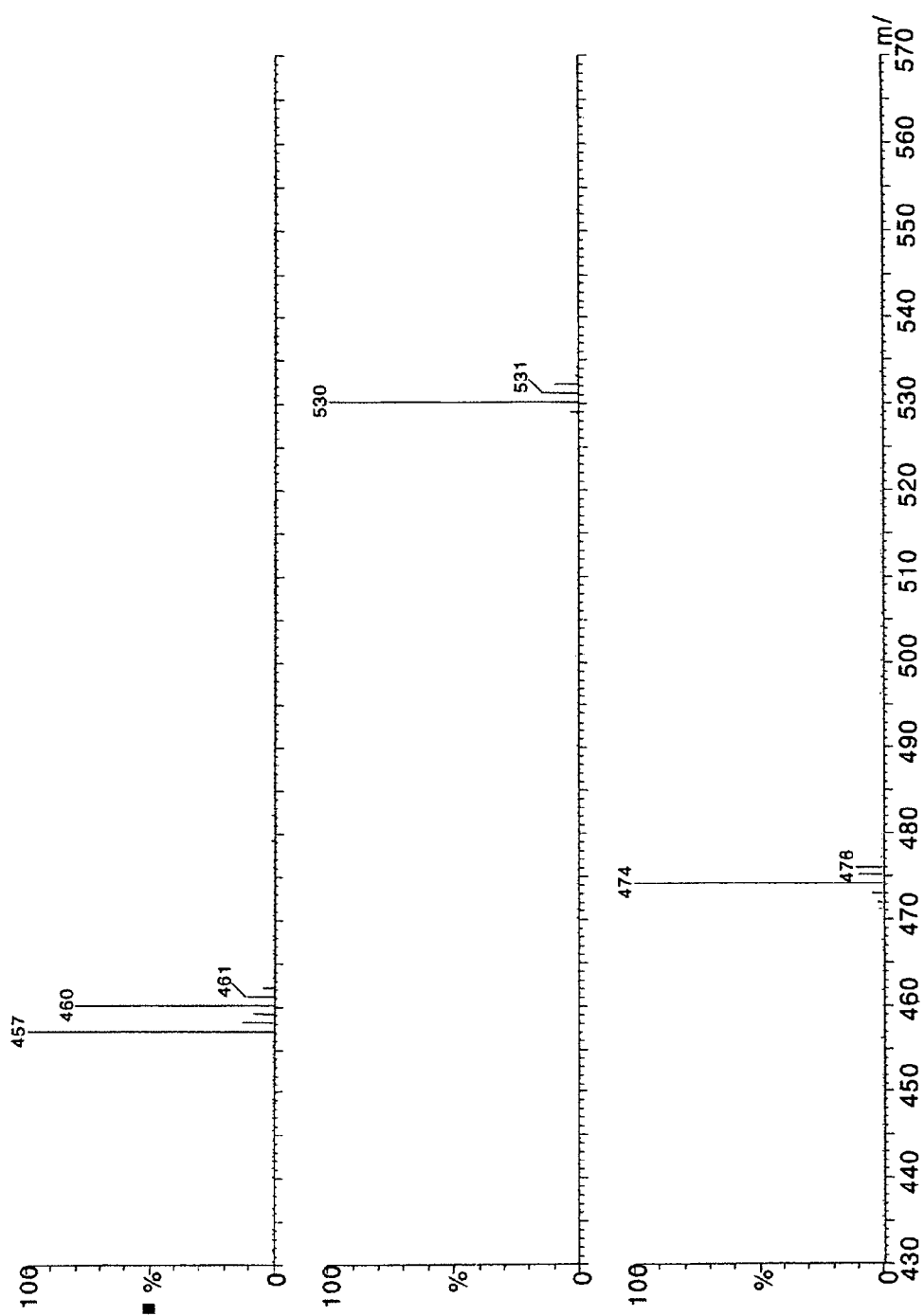
FIG. 1B—Acetaminophen mass spectra for the three most abundant components from the total ion chromatograph of FIG. 1A (at 2.08 min (top), at 0.92 min (middle), at 4.39 min (bottom), respectively).

FIG. 1A shows the total ion chromatogram (MS) of the neutral loss scanning of 129 Da obtained for the reaction mixture. Three major components were detected in the MS designated as A (2.08 min), B (0.92 min) and C (4.39 min), based on the peak intensity. The MS spectra for the three components were evaluated as is shown in FIG. 1B. Component A showed a doublet of equal intensities at m/z 457 and 460 Da, respectively (FIG. 1B, top). This MS doublet signature indicated the formation of an adduct of the reactive metabolite NAPQI. In contrast, the spectra of components B (0.92 min) and C (4.39 min) (FIG. 1B, middle and bottom respectively) displayed only singlets at m/z 474 and 530 Da, respectively. Absence of an isotopic doublet indicated that both B and C were non-reactive metabolites.

EXAMPLE 3

Carbamazepine

Carbamazepine was selected to demonstrate the applicability of the method of the invention to the detection of reactive arene oxide metabolites. The reaction of carbamzepine with glutathione is outlined in Scheme 2.

Scheme 2

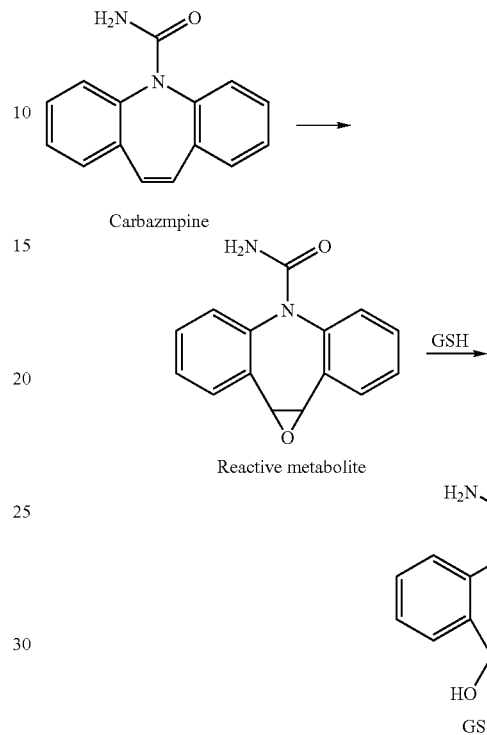

Carbazmpine

Reactive metabolite

GSH adduct

Figure 2A:
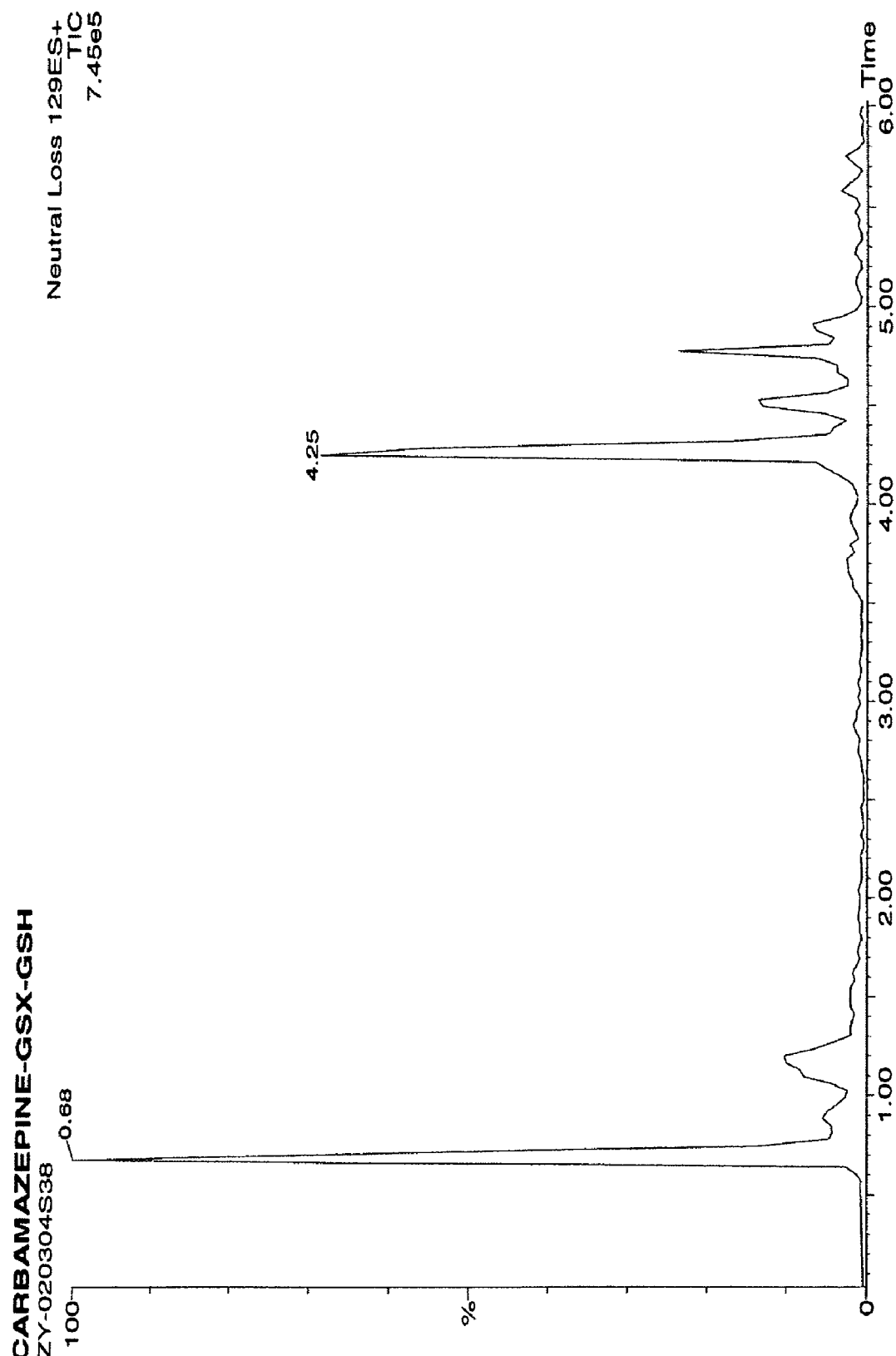
FIG. 2A—Carbamazepine total ion chromatogram of neutral loss scanning of 129 Da.
Figure 2B:
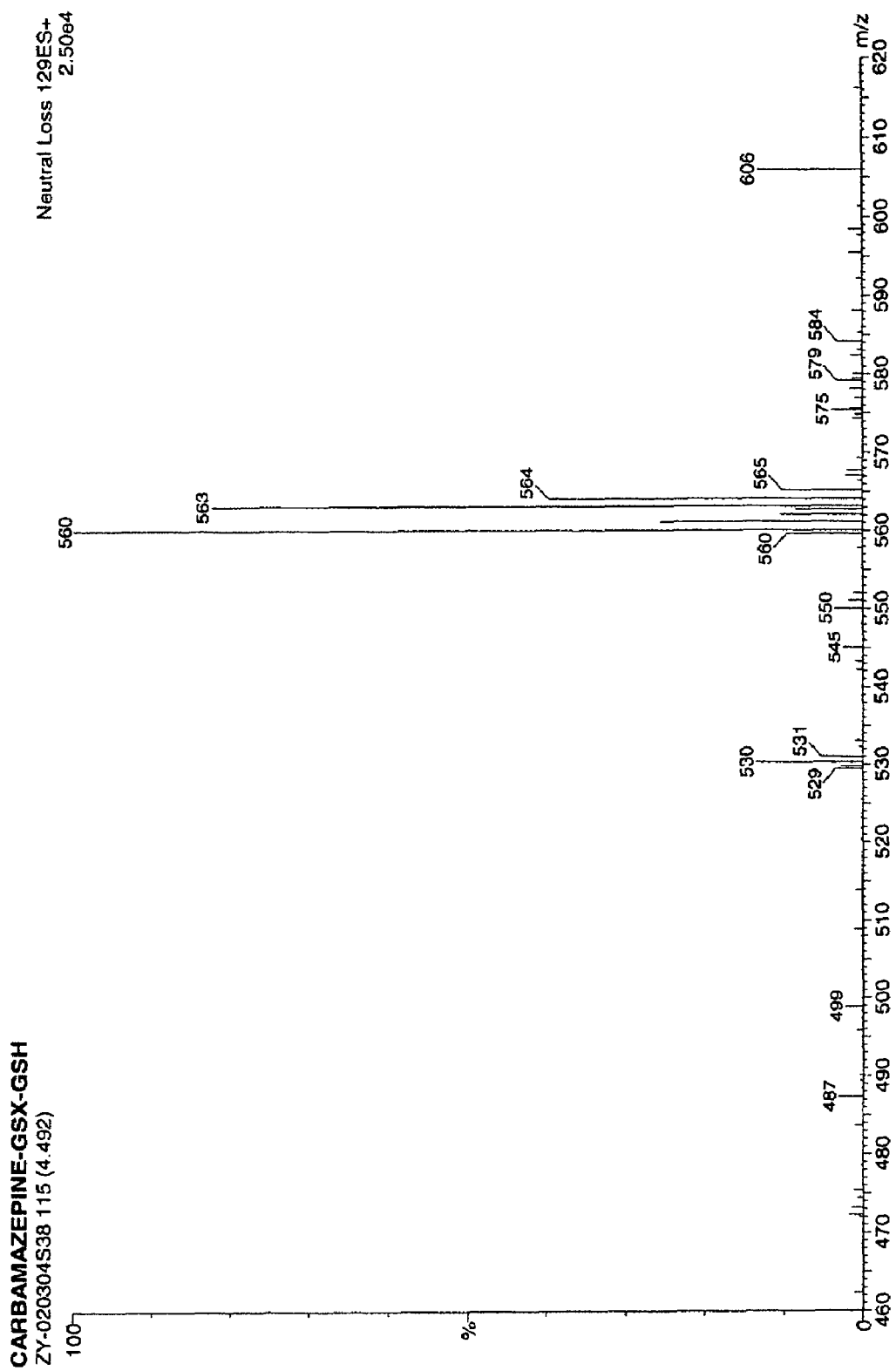
FIG. 2B—Carbamazepine mass spectrum for the most abundant component from the total ion chromatograph (at 4.5 min).

FIG. 2A shows the total ion chromatogram (MS) of the neutral loss scanning of 129 Da obtained for the reaction mixture. Several components showed positive response to the neutral scan, but only one component at a retention time of 4.5 min displayed the characteristic doublet at m/z 560 and 563 Da (FIG. 2B).

EXAMPLE 4

Diclofenac

Diclofenac was selected as to demonstrate the applicability of the method of the invention to the detection of reactive quinone imine metabolites. The reaction of diclofenac with glutathione is outlined in Scheme 3.

Scheme 3

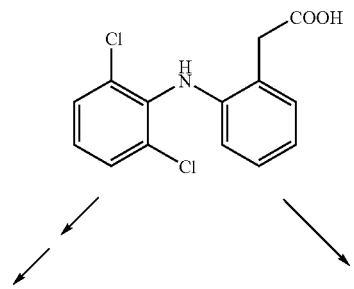

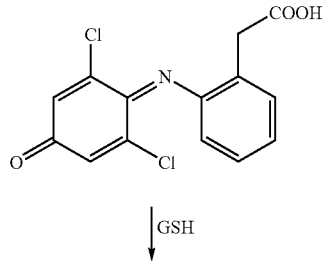
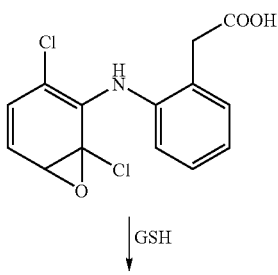

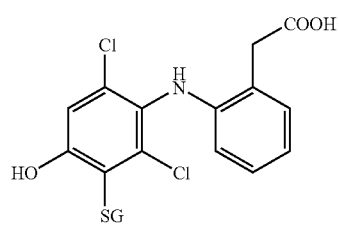
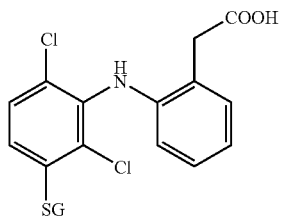

Figure 3A:
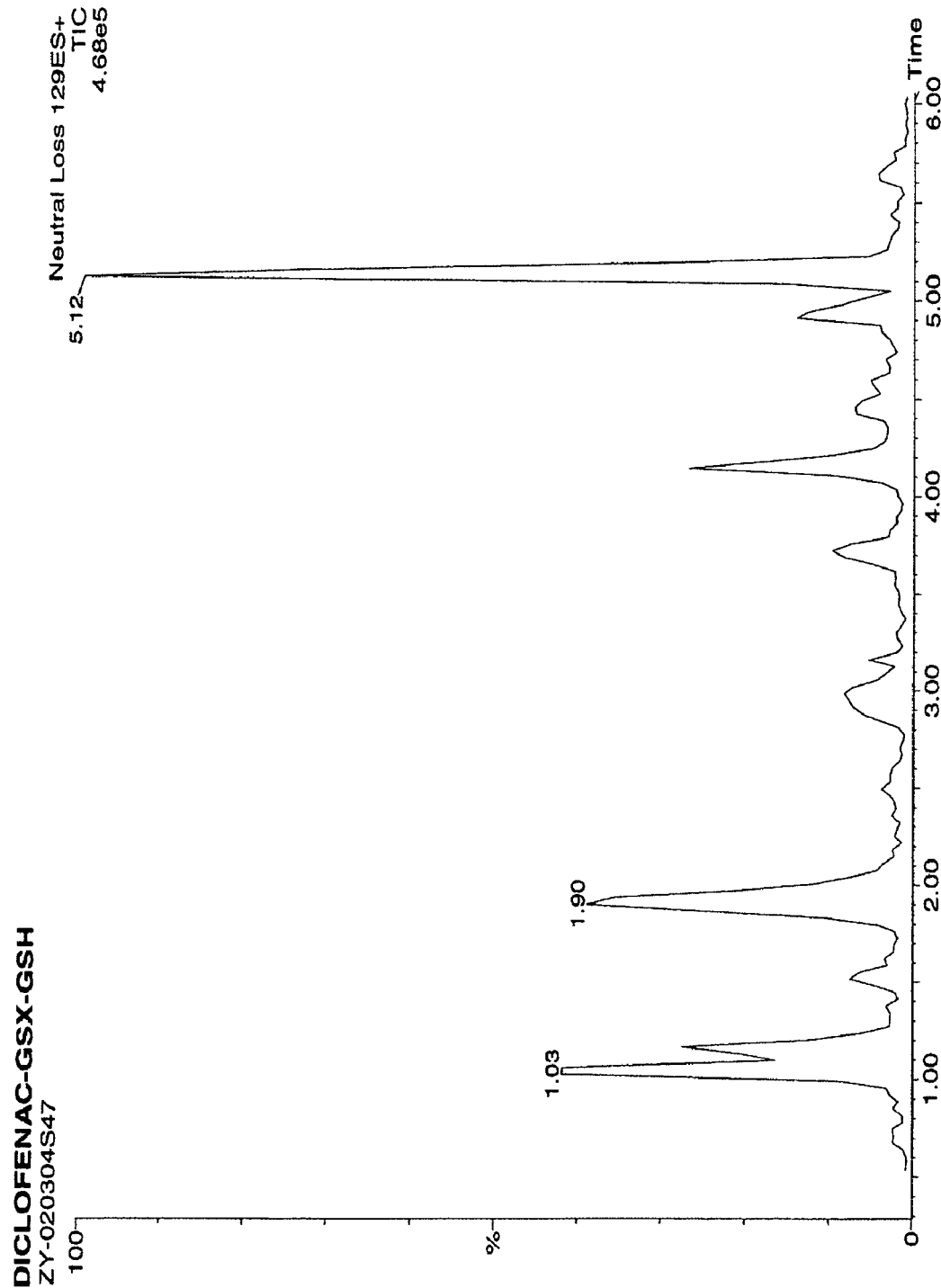
FIG. 3A—Diclofenac total ion chromatogram of neutral loss scanning of 129 Da.
Figure 3B:
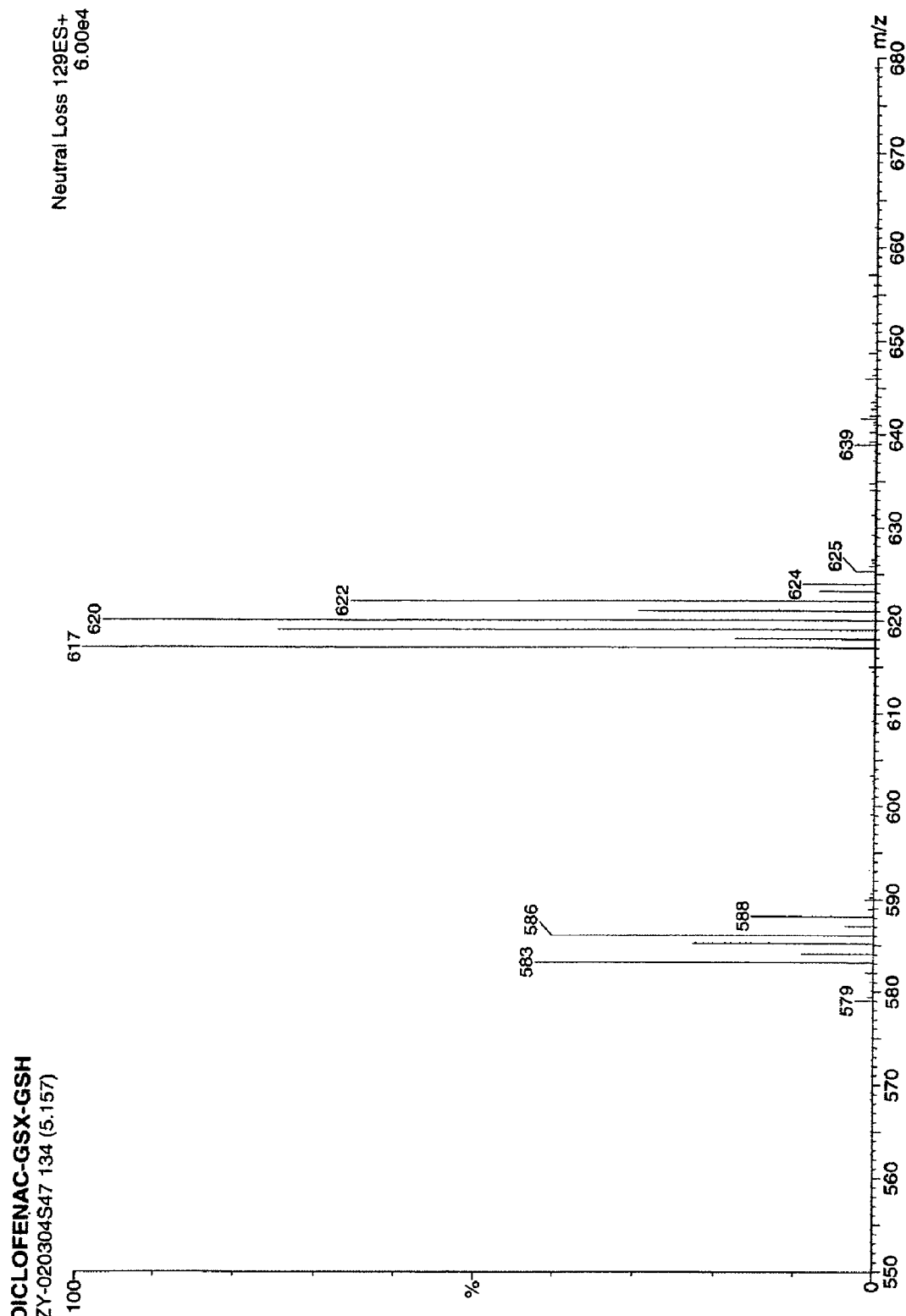
FIG. 3B—Diclofenac mass spectrum for the most abundant component from the total ion chromatograph (at 5.12 min).

FIG. 3A shows the total ion chromatogram (MS) of the neutral loss scanning of 129 Da obtained for the reaction mixture. Several components showed positive response to the neutral scan, but only one peak at retention time of 5.12 min displayed two pairs of characteristic doublets (FIG. 3B), one pair at m/z 583 and 586 Da (FIG. 4B), and the other at m/z 617 and 620. The data suggested that two reactive metabolites were co-eluted from the column.

EXAMPLE 5

Clozapine

Clozapine was selected to demonstrate the applicability of the method of the invention to the detection of reactive nitrenium ion metabolites. The reaction of clozapine with glutathione is outlined in Scheme 4.

Scheme 4

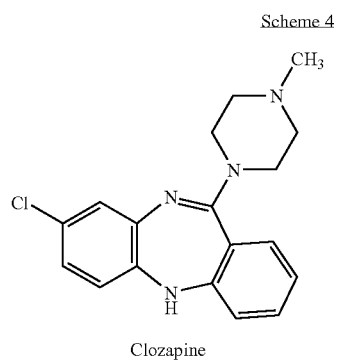

Clozapine

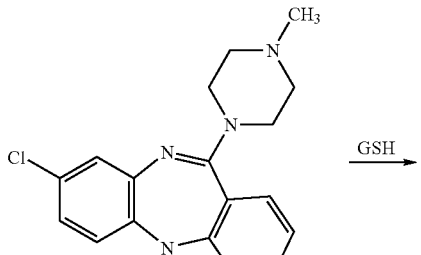

Reactive metabolite

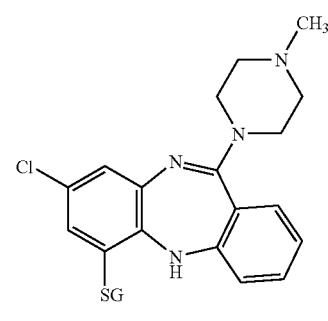

GSH adduct

Figure 4A:
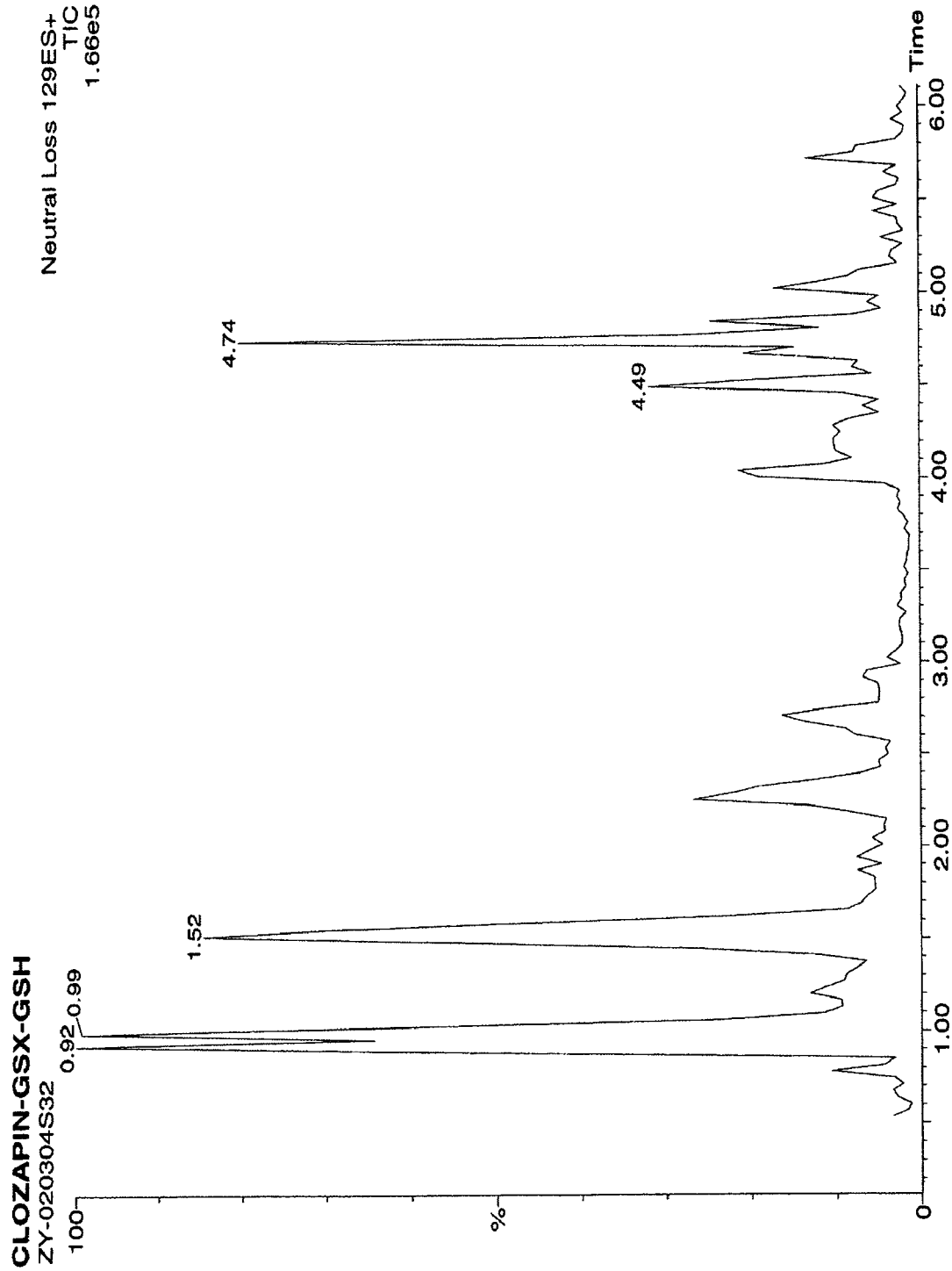
FIG. 4A—Clozapine total ion chromatogram of neutral loss scanning of 129 Da.
Figure 4B:
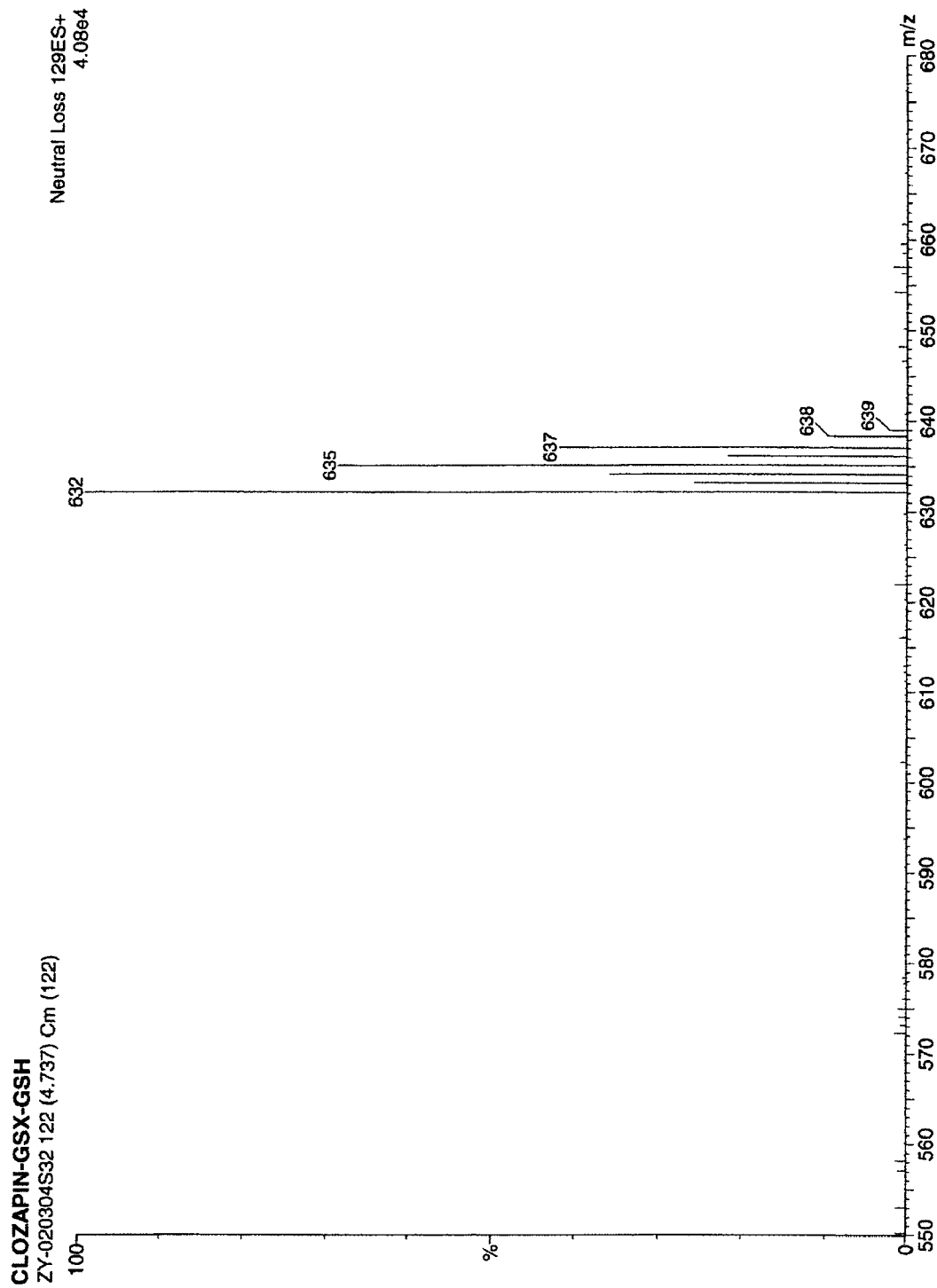
FIG. 4B—Clozapine mass spectrum for the most abundant component from the total ion chromatograph (at 4.74 min).

FIG. 4A shows the total ion chromatogram (MS) of the neutral loss scanning of 129 Da obtained for the reaction mixture. Several components showed positive response to the neutral scan, but only one component at a retention time of 4.74 min displayed characteristic doublet at m/z 632 and 635 Da (FIG. 4B).

EXAMPLE 6

4-Hydroxyestrone

4-Hydroxyestrone was selected to demonstrate the applicability of the method of the invention to the detection of reactive quinone methide metabolites. The reaction of 4-hydroxyestrone with glutathione is outlined in Scheme 5.

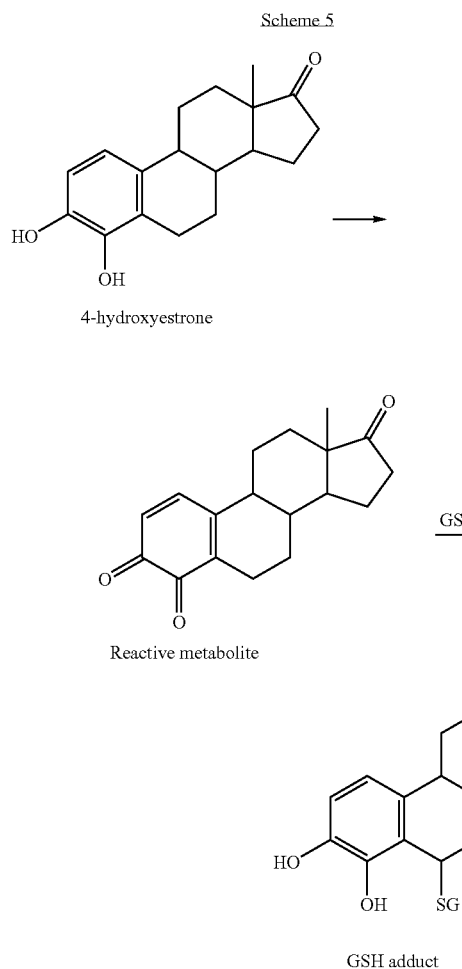

Figure 5A:
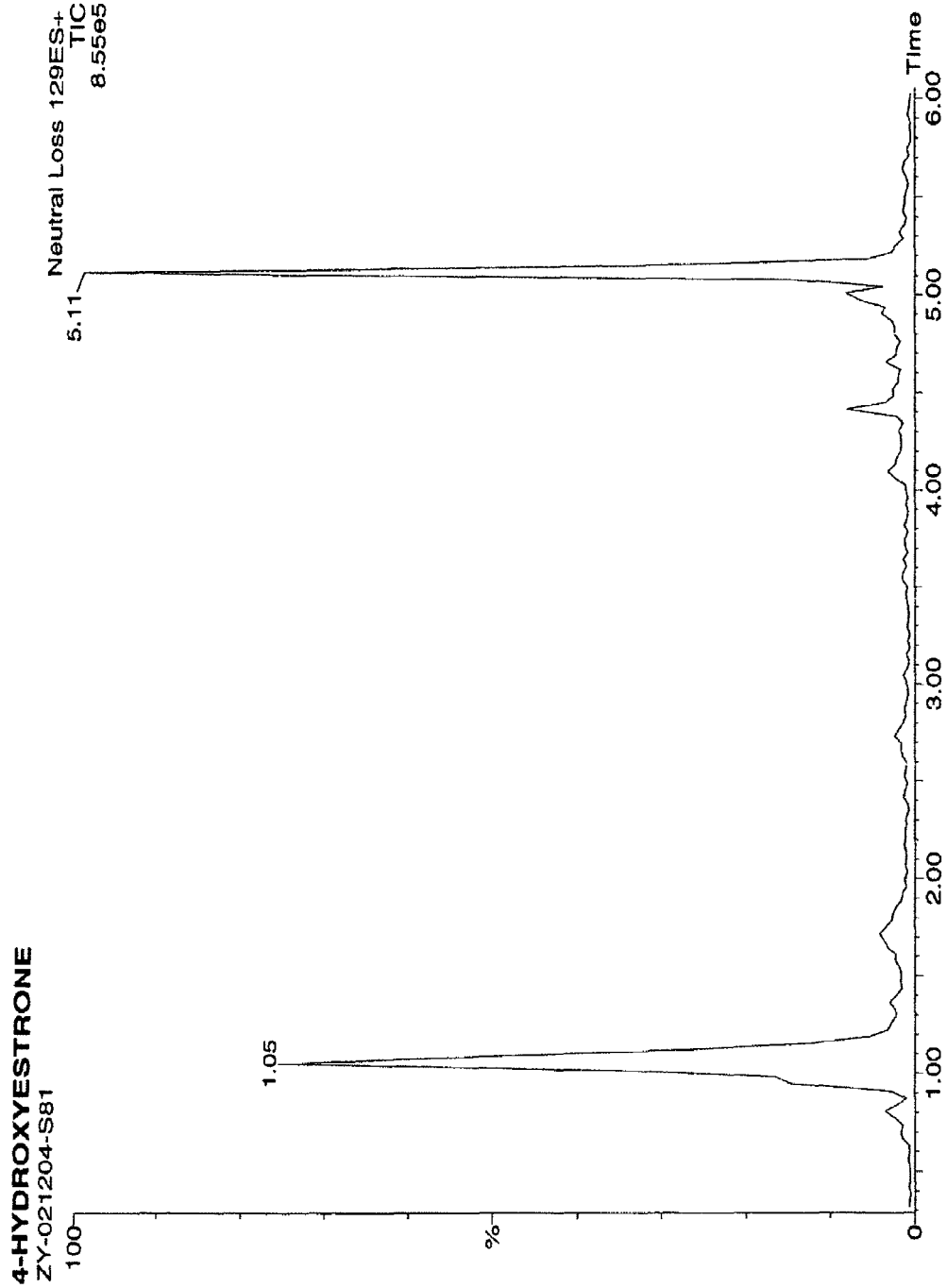
Figure 5B:
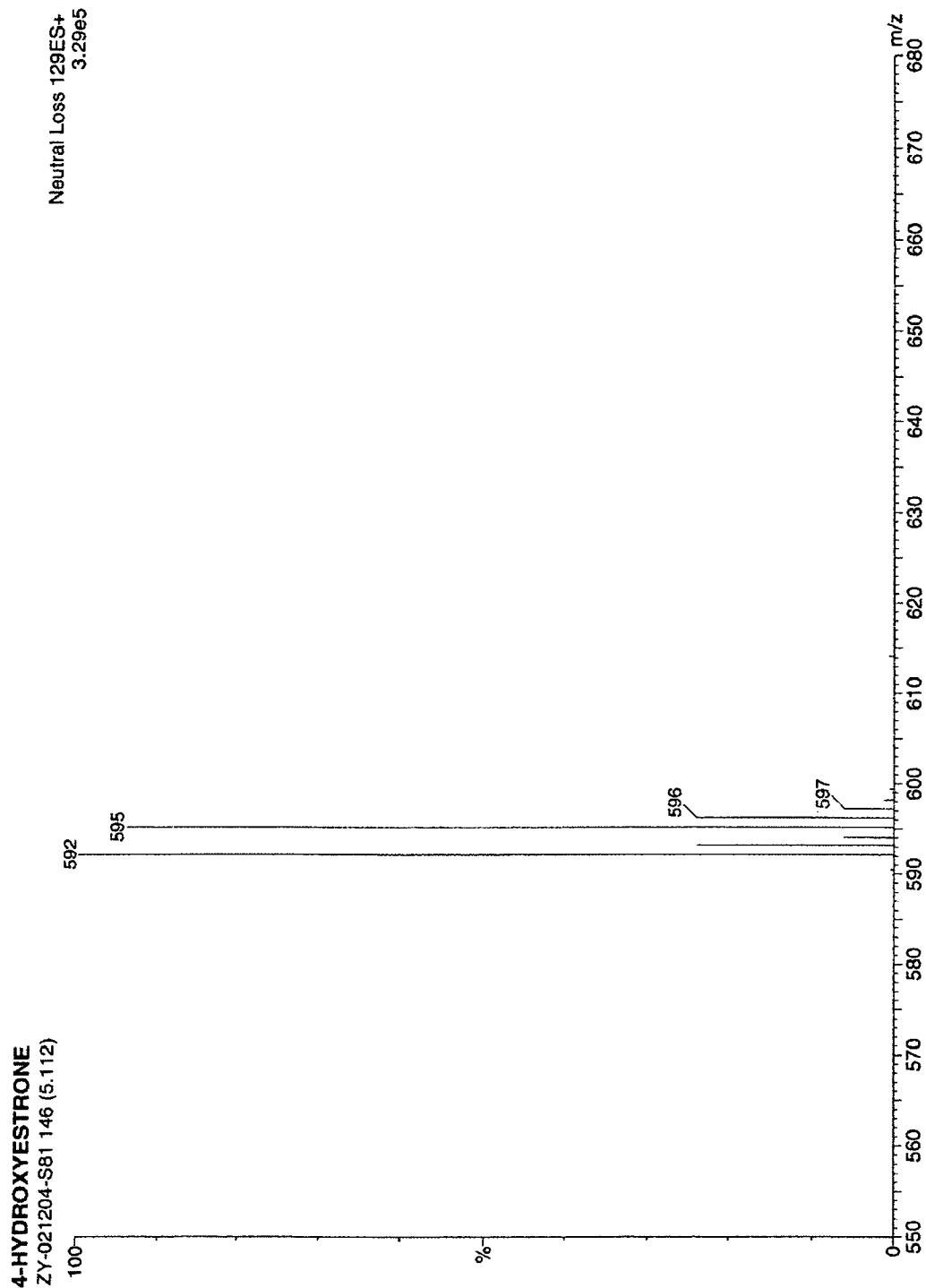

FIG. 5A shows the total ion chromatogram (MS) of the neutral loss scanning of 129 Da obtained for the reaction mixture. Two components showed positive response to the neutral scan, but only one component at a retention time of 5.11 min displayed characteristic doublet at m/z 592 and 595 Da (FIG. 5B).

EXAMPLE 7

3-Methylindole

3-Methylindole was selected to demonstrate the applicability of the method of the invention to the detection of reactive indolenines metabolites. The reaction of 3-methylindole with glutathione is outlined in Scheme 6.

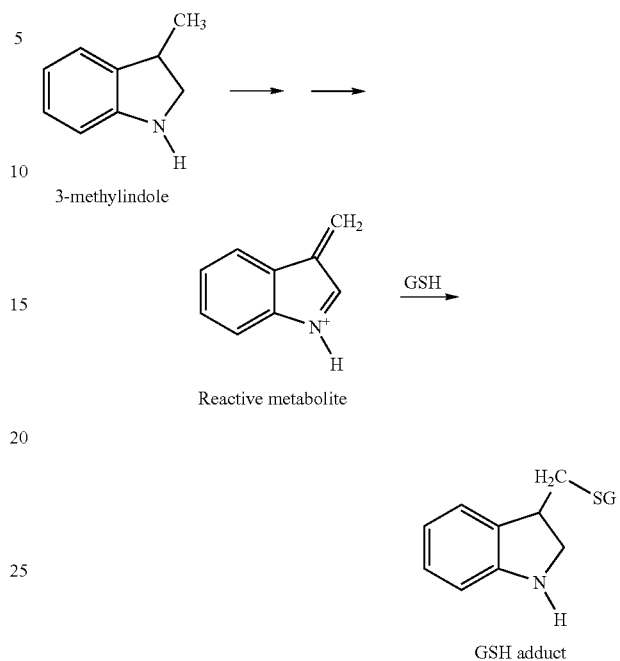

Figure 6A:
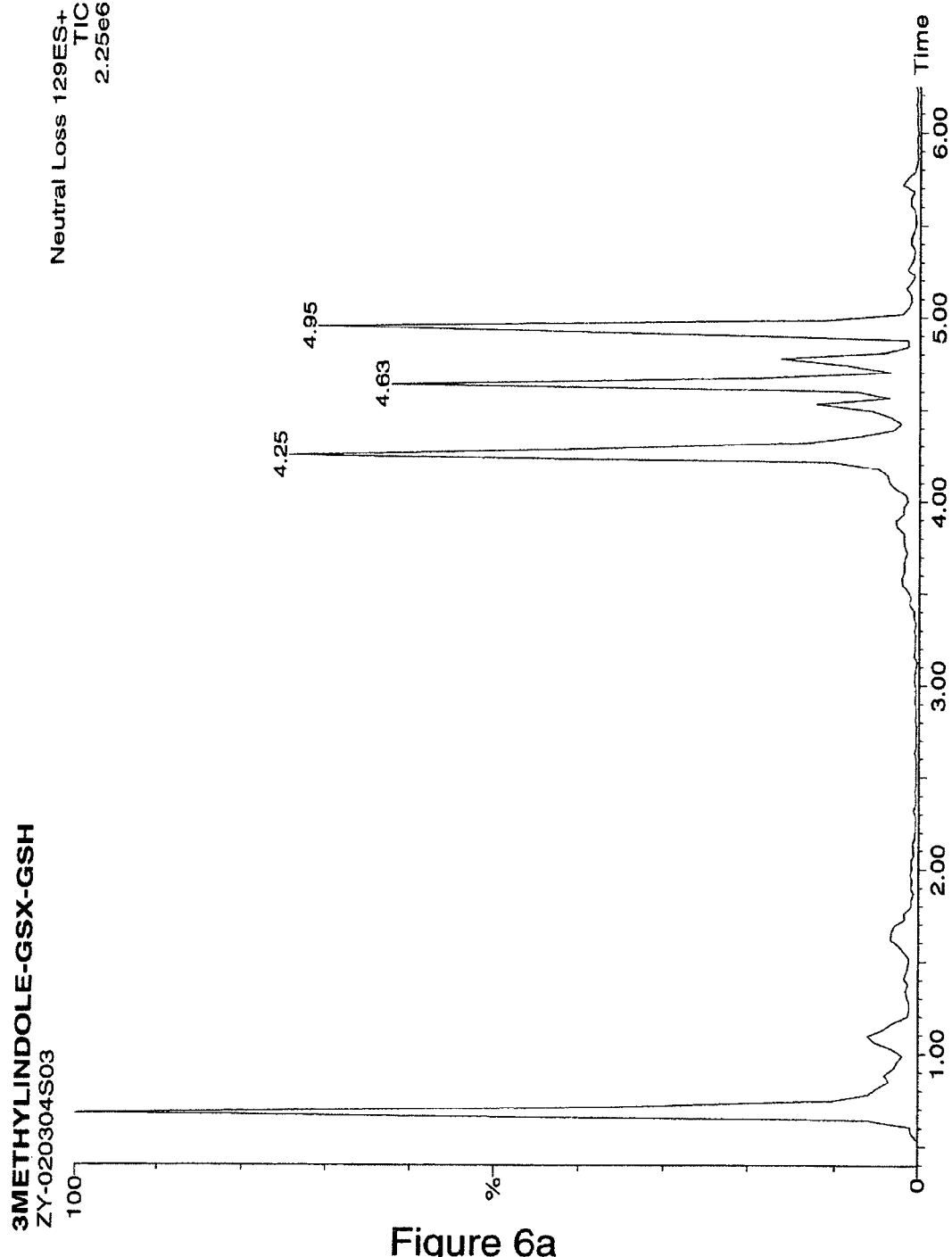
Figure 6B:
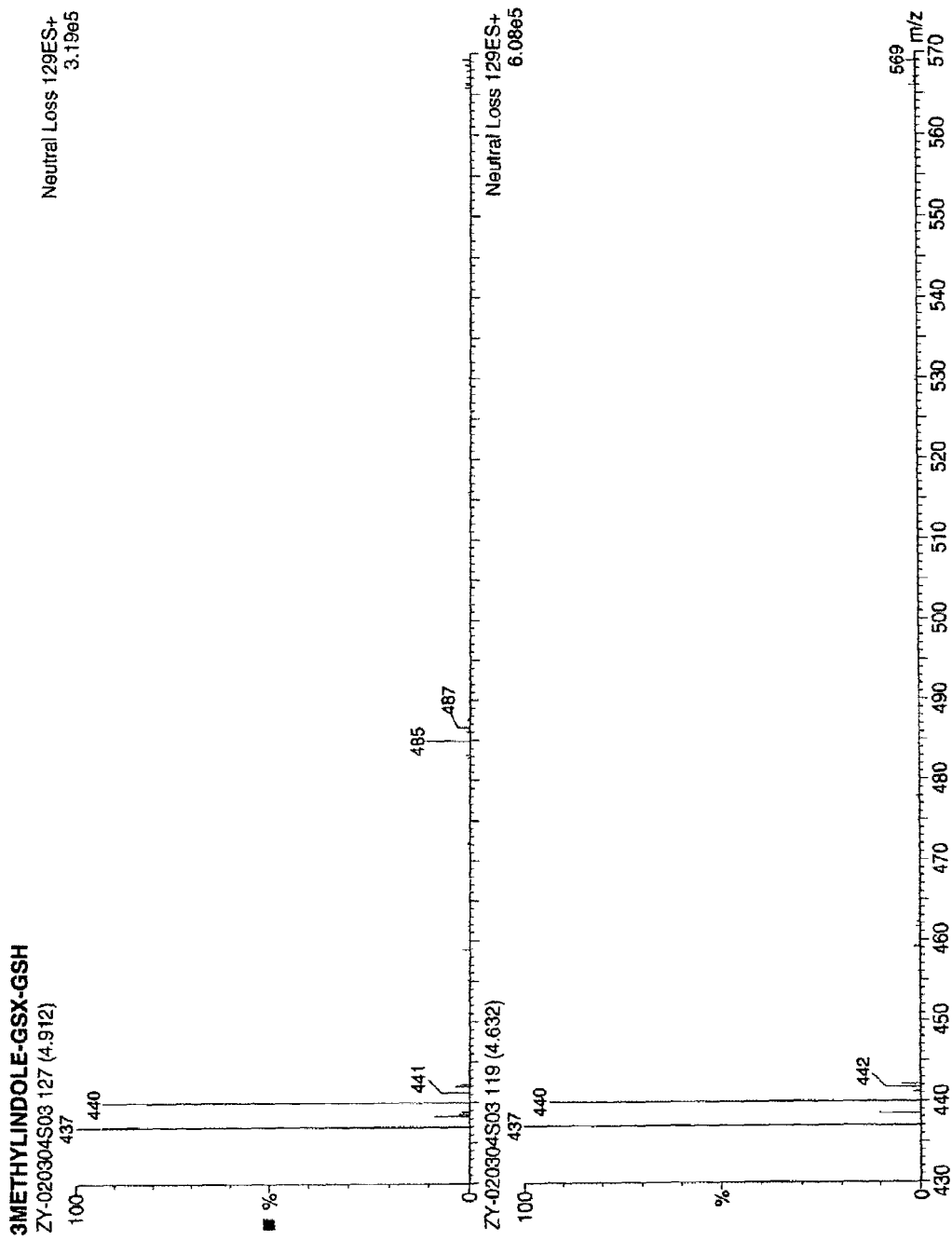

FIG. 6A shows the total ion chromatogram (MS) of the neutral loss scanning of 129 Da obtained for the reaction mixture. Several components showed positive response to the neutral scan, but only two components at retention times of 4.63 min and 4.95 min displayed a characteristic doublet at m/z 437 and 440 Da (FIG. 6B).

EXAMPLE 8 p-Cresol p-Cresol was selected to demonstrate the applicability of the method of the invention to the detection of reactive quinone metabolites. The reaction of p-cresol with glutathione is outlined in Scheme 7.

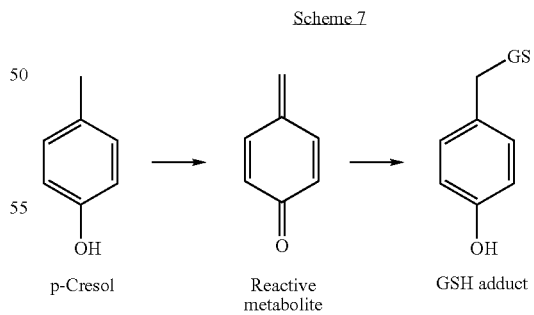

Figure 7A:
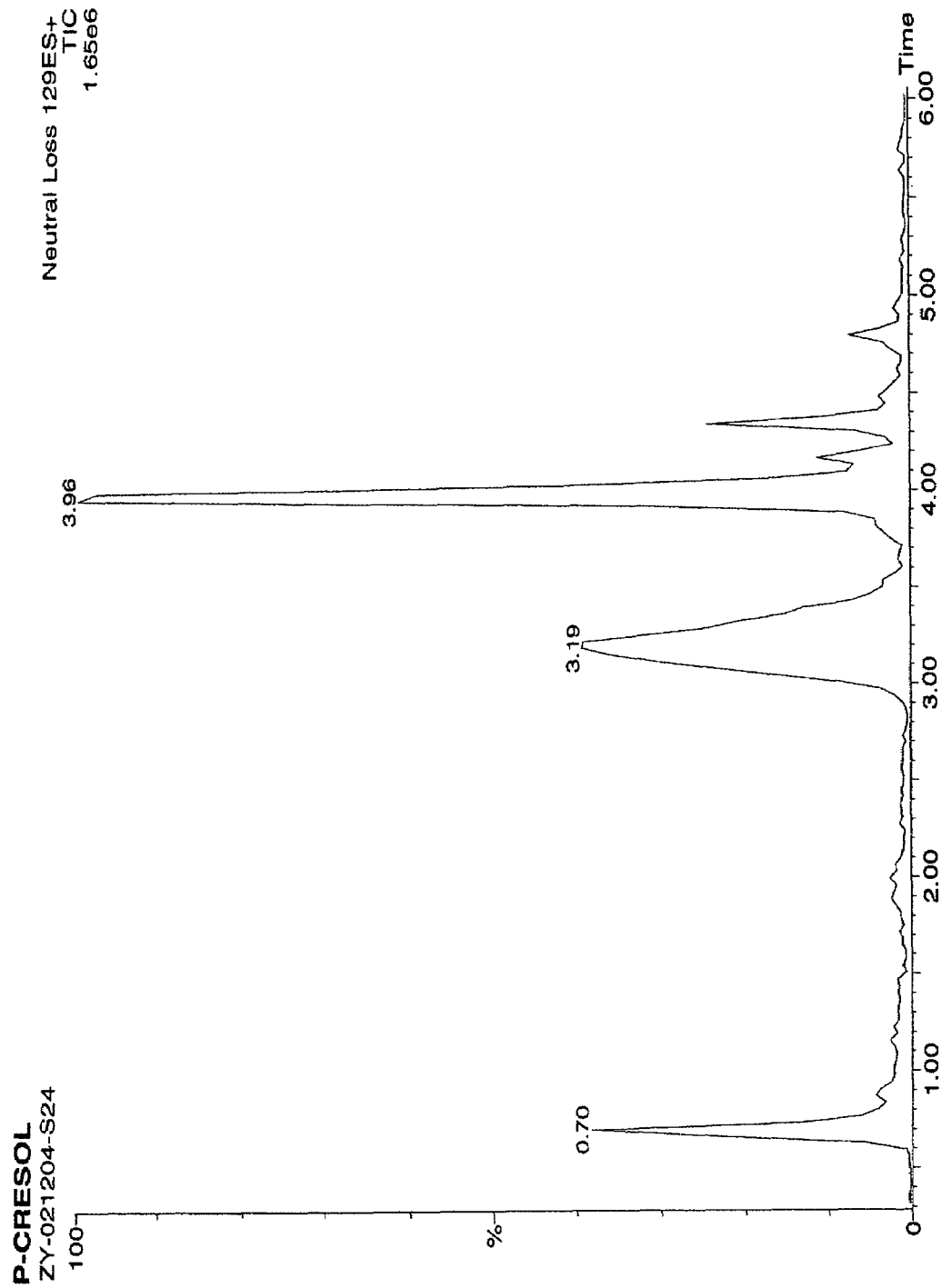
Figure 7B:
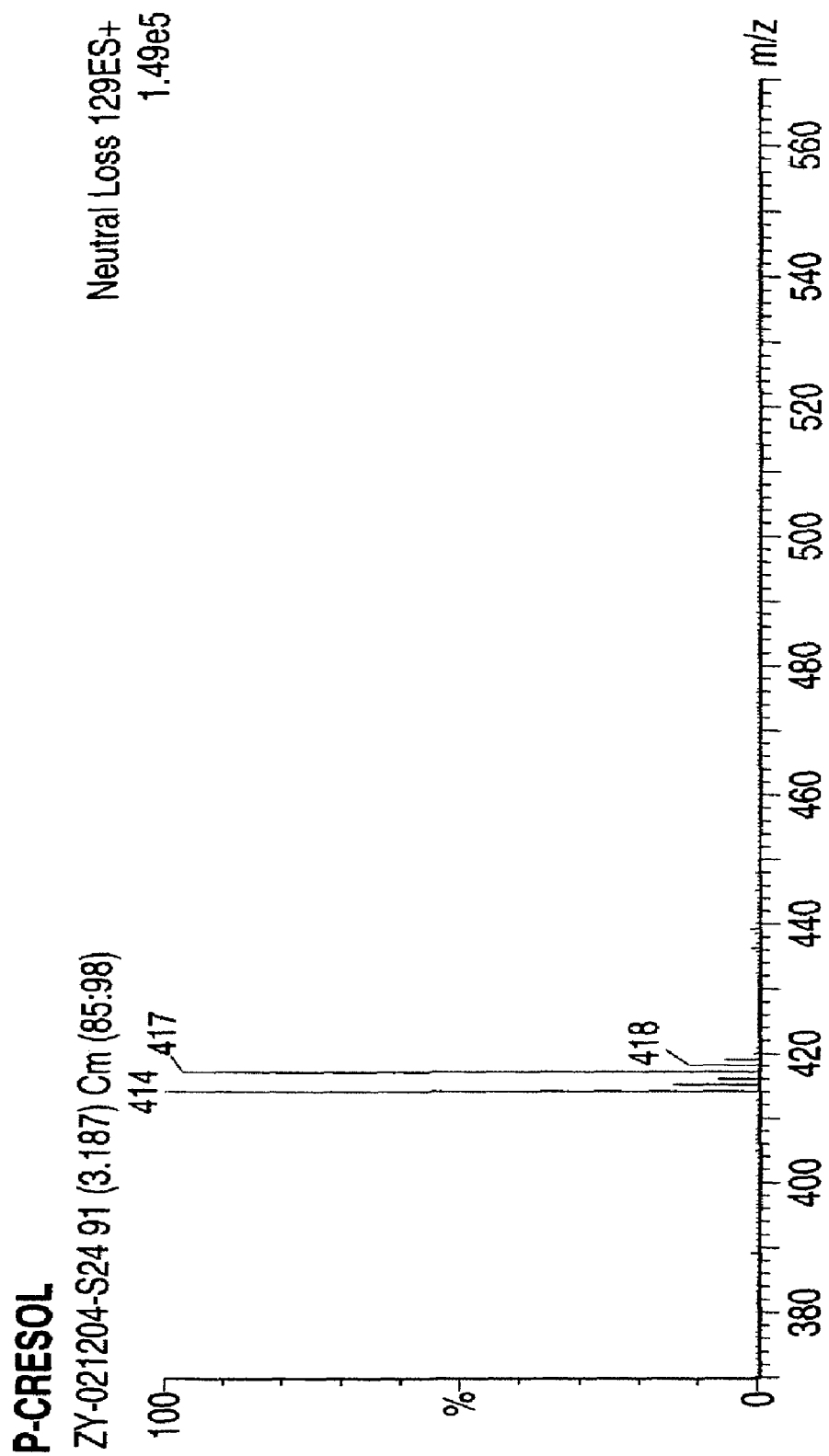

FIG. 7A shows the total ion chromatogram (MS) of the neutral loss scanning of 129 Da obtained for the reaction mixture. Several components showed positive response to the neutral scan, but only one component at a retention time of 3.96 min displayed a characteristic doublet at m/z 430 and 433 Da (FIG. 7B).

EXAMPLE 9

Omeprazole

Omeprazole was selected to demonstrate the applicability of the method of the invention to the detection of reactive sulfenic acid metabolites. The reaction of omeprazole with glutathione is outlined in Scheme 8.

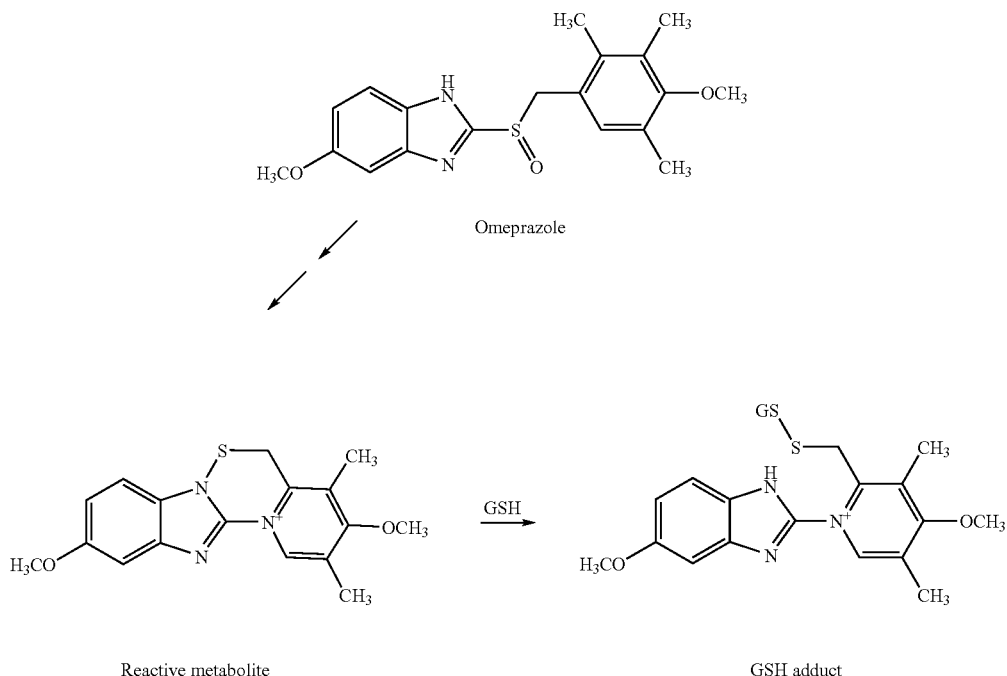

Figure 8A:
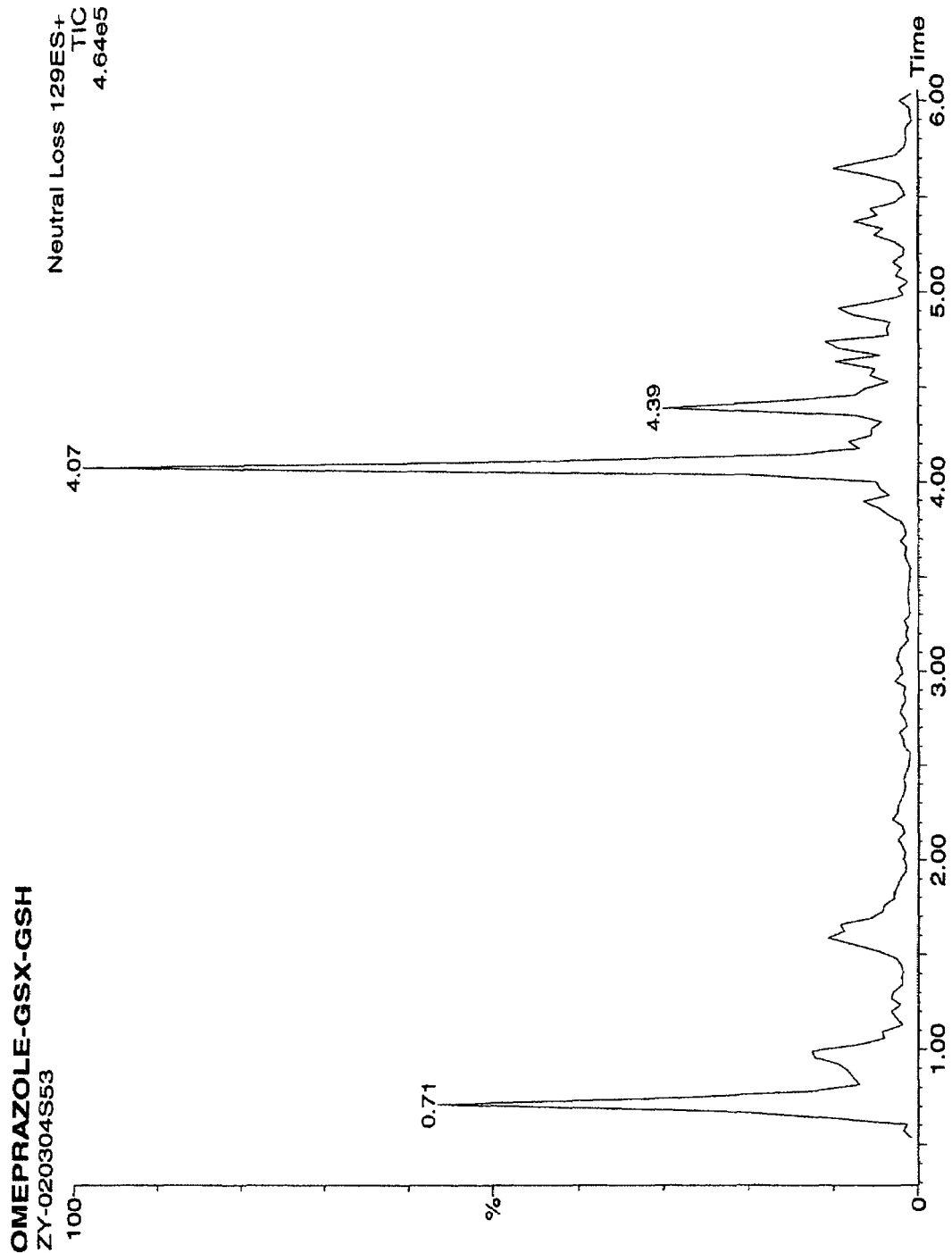
FIG. 8A—Omeprazole total ion chromatogram of neutral loss scanning of 129 Da.
Figure 8B:
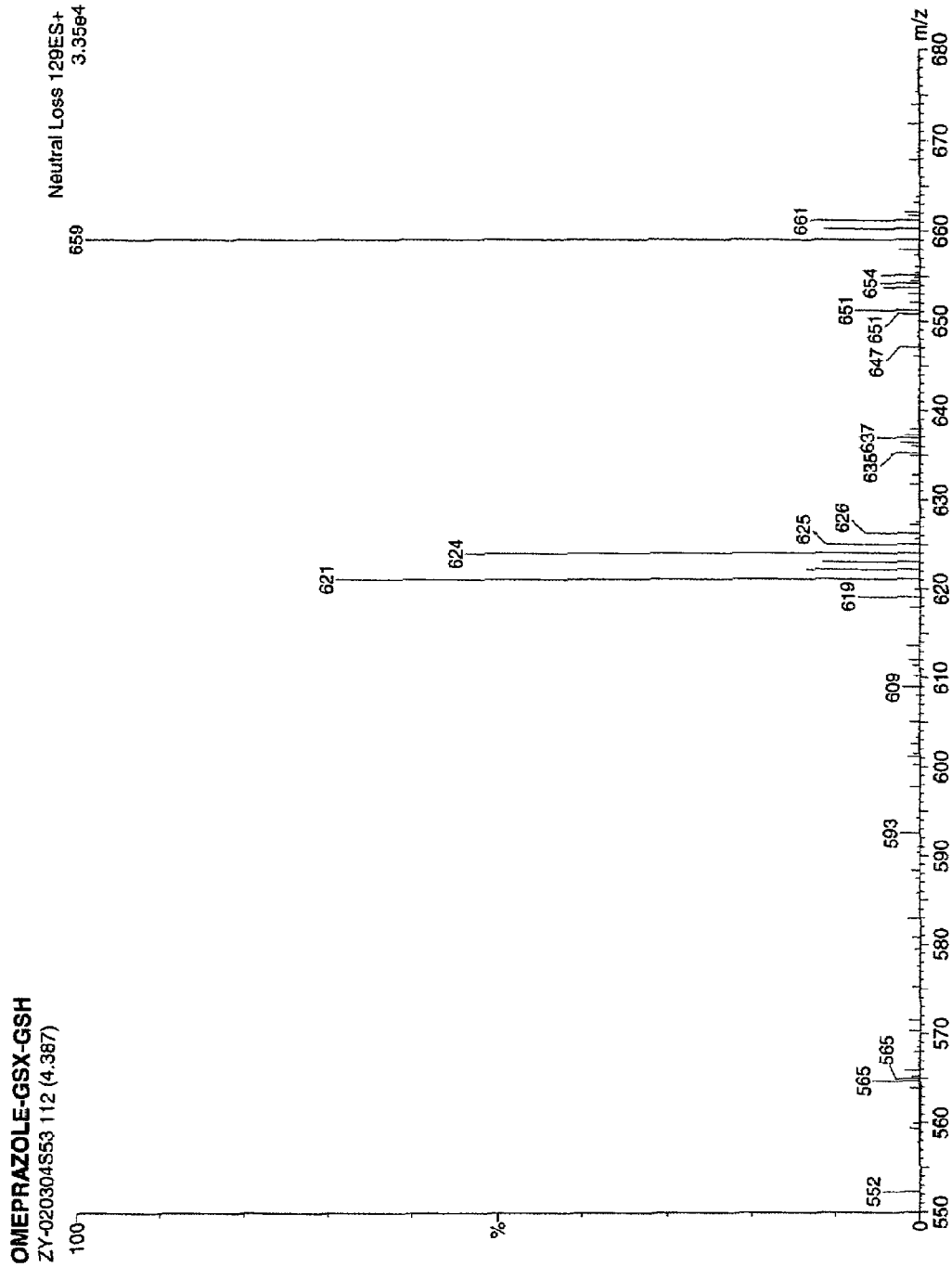
FIG. 8B—Omeprazole mass spectrum for the most abundant component from the total ion chromatograph (at 4.39 min).

FIG. 8A shows the total ion chromatogram (MS) of the neutral loss scanning of 129 Da obtained for the reaction mixture. Several components showed positive response to the neutral scan, but only one component at a retention time of 4.39 min displayed a characteristic doublet at m/z 621 and 624 Da (FIG. 8B).

EXAMPLE 10

Felbamate

Felbamate was selected to demonstrate the applicability of the method of the invention to the detection of reactive atropaldehyde metabolites. The reaction of felbamate with glutathione is outlined in Scheme 9.

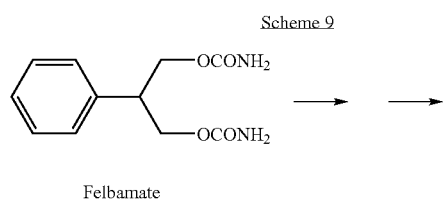

Figure 9A:
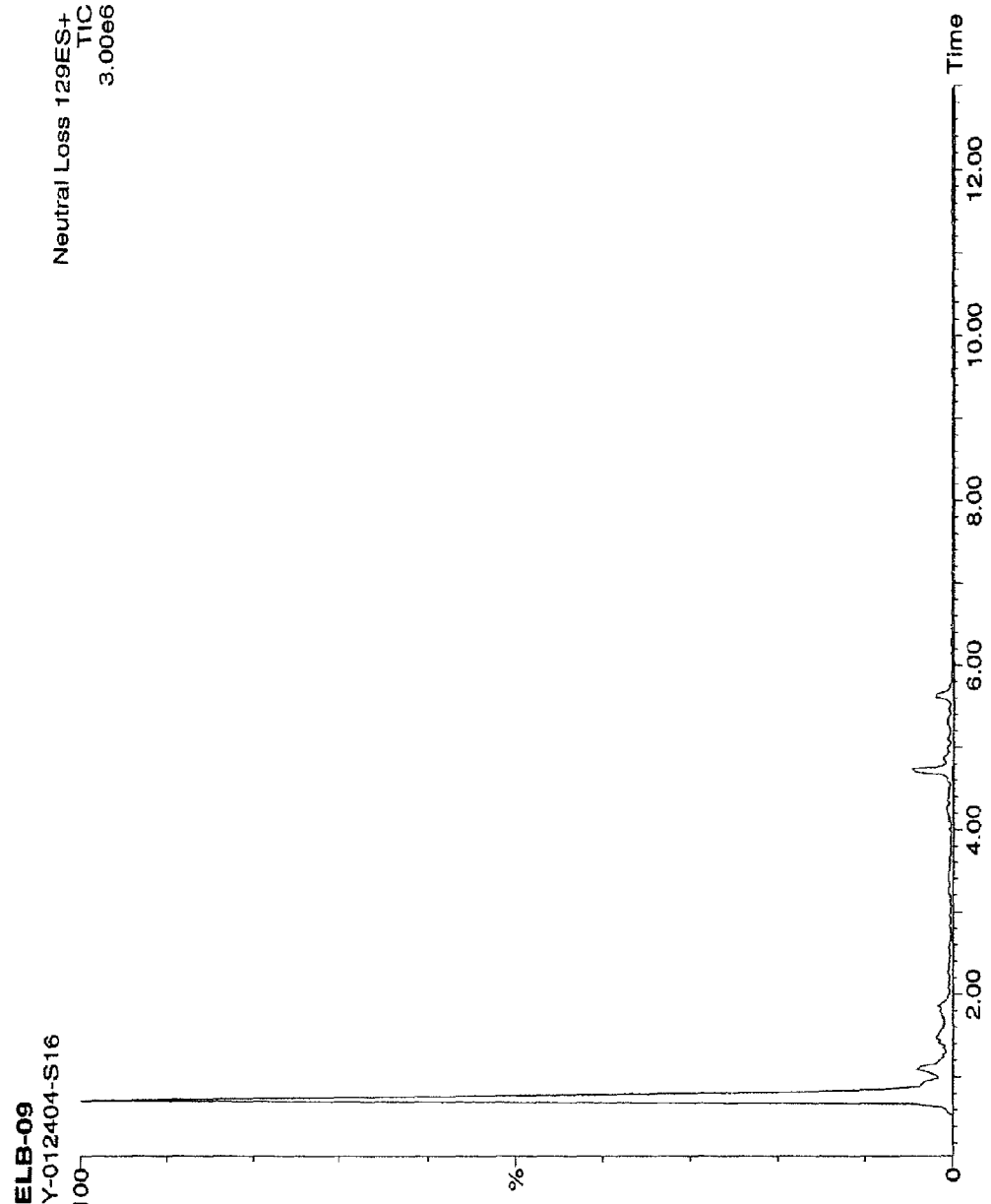
FIG. 9A—Felbamate total ion chromatogram of neutral loss scanning of 129 Da.
Figure 9B:
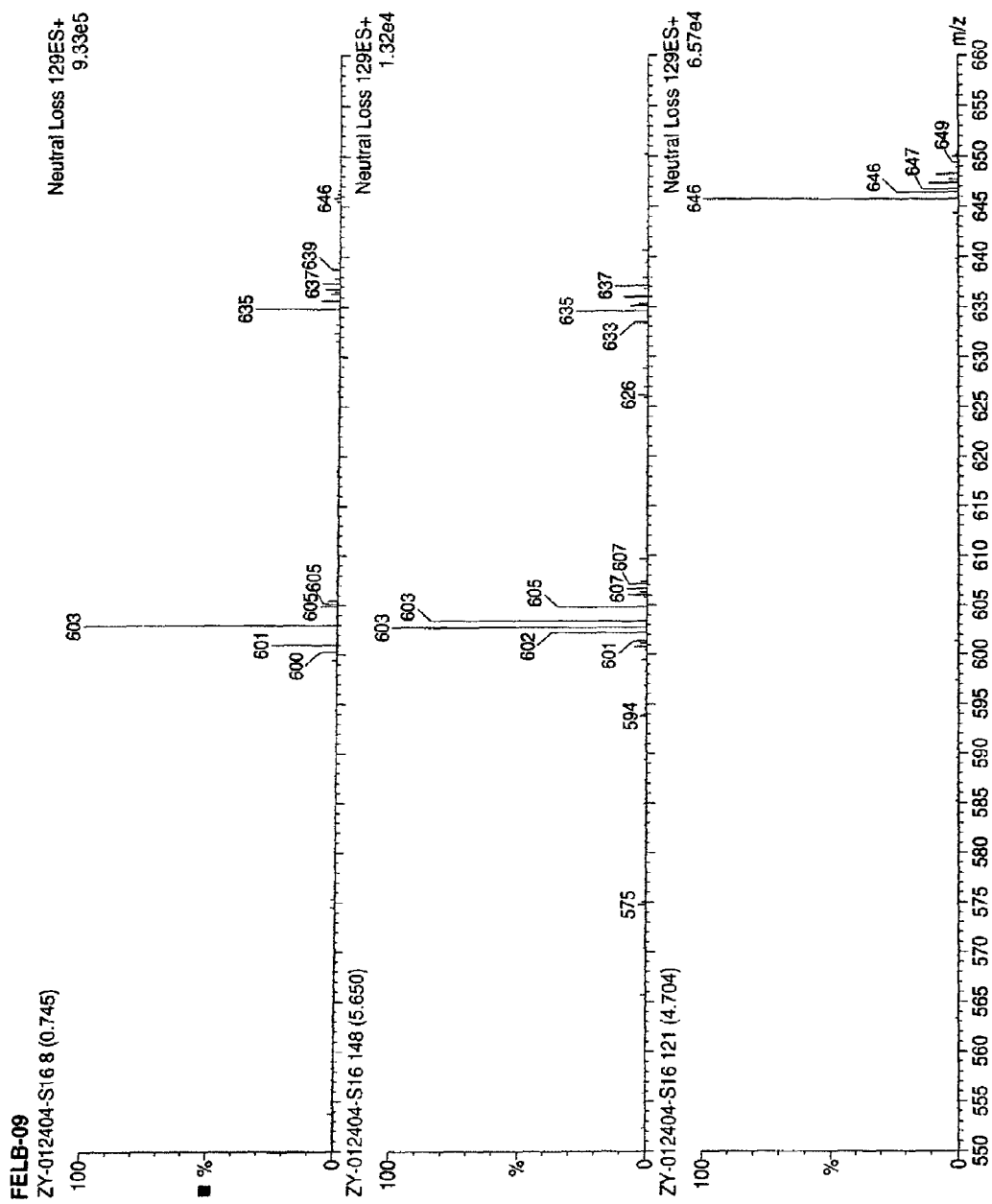
FIG. 9B—Felbamate mass spectra for the most abundant component from the total ion chromatograph (at 0.75 min (top), at 5.65 min (middle), at (4.70 min (bottom), respectively).

FIG. 9A shows the total ion chromatogram (MS) of the neutral loss scanning of 129 Da obtained for the reaction mixture, but none of them displayed a characteristic doublet (FIG. 9B), suggesting that no reactive metabolites were formed. This could be explained by the fact that convertion of felbamate to the reactive metabolite is not catalyzed by CYPs, but likely by non-CYP enzymes such as esterase and adehyde dehydrogenase (22); both esterases and adehyde dehydrogenase are usually absent in human liver microsomes.

EXAMPLE 11

FIA-MS/MS detection of Reactive Metabolites

For rapidly screening for reactive metabolites, flow injection was used to replace liquid chromatography to reduce analysis time. 4-Hydroxyestrone was selected as a test compound to demonstrate the applicability of the method of the present invention to the detection of reactive metabolite within 30 sec.

Figure 10A:
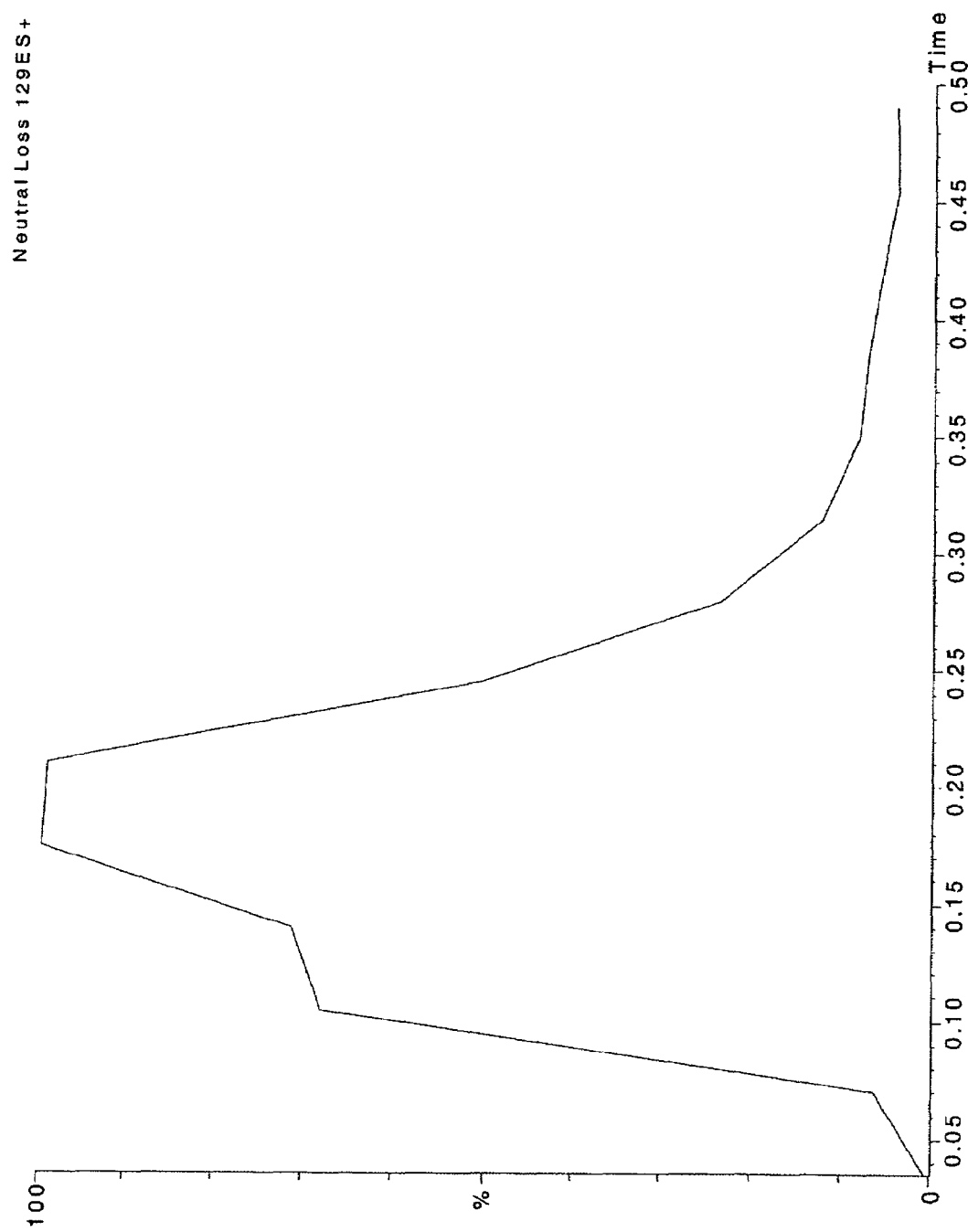
FIG. 10A—FIA-MS/MS Total ion chromatogram of neutral loss scanning of 129 Da.
Figure 10B:
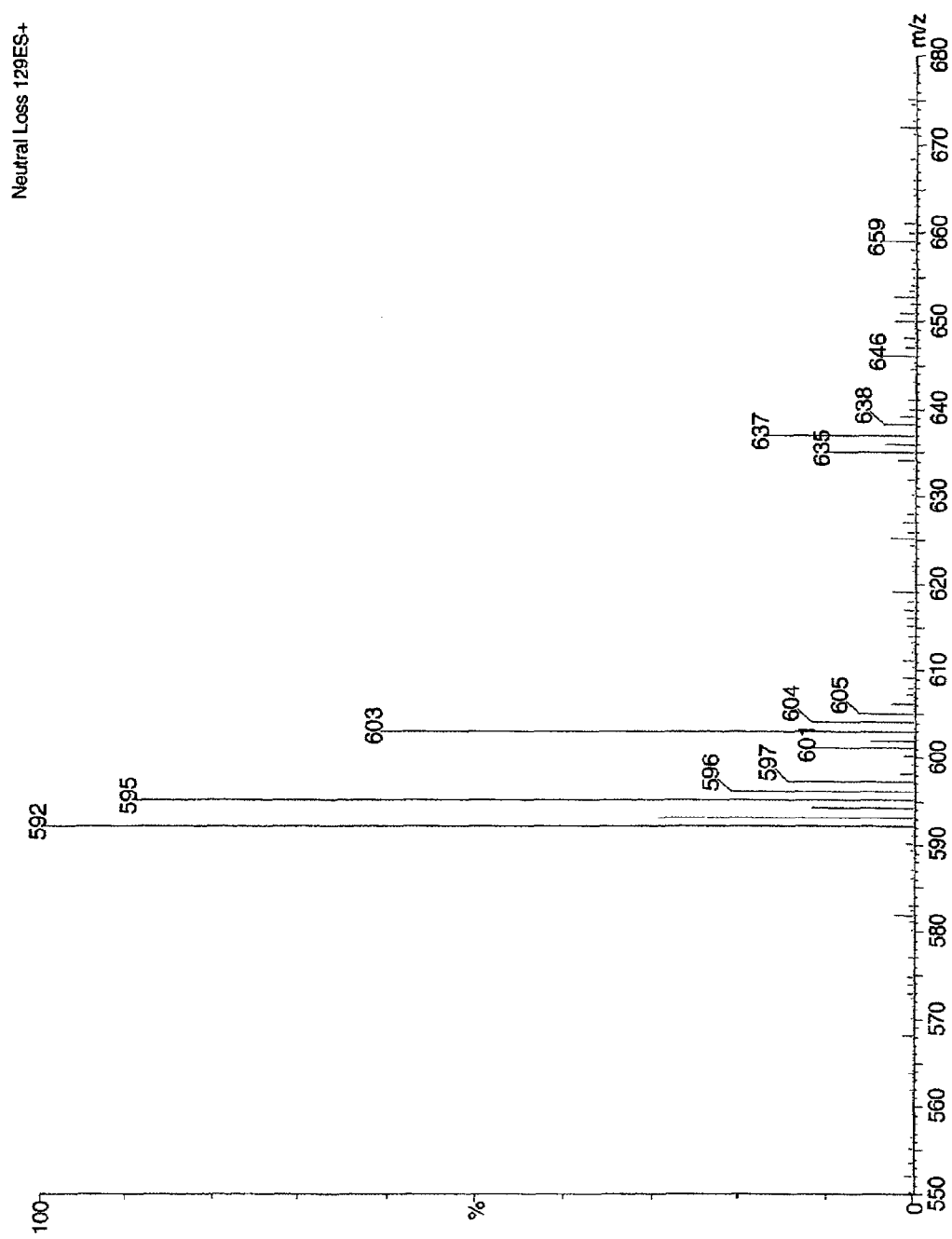
FIG. 10B—Mass spectrum for the most abundant component from the total ion chromatograph.

FIG. 10A shows the total ion chromatogram (MS) of the neutral loss scanning of 129 Da obtained for the reaction mixture. The entire analytical process was completed within 30 sec, and the reactive metabolite was detected in the MS (FIG. 10B), as indicated by the characteristic doublet at m/z 592 and 595 Da, While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for detecting reactive metabolites of a drug candidate comprising
   (a) incubating a drug candidate with a mixture comprising a non-labeled trapping agent that is γ-glutamyl-cystein-glycin, an isotopically-labeled trapping agent that is γ-glutamyl-cystein-glycin that is labeled at 1 to 17 positions with at least one isotope selected from the group consisting of $^{13}C$, $^{15}N$, $^{18}O$, $^{2}H$, $^{3}H$, $^{34}S$, and a drug metabolizing enzyme; and
   (b) detecting one or more said reactive metabolites by detecting corresponding isotopic doublets in a neutral loss mass spectrum of a product of step (a), wherein the doublet differs in mass by the difference in mass between the non-labeled trapping agent and the isotopically labeled trapping agent.

2. The method of claim 1, wherein the isotopically-labeled trapping agent is γ-glutamyl-cystein-glycin-$^{13}C2$-$^{15}N$.

3. The method of claim 2, wherein the molar ratio of the non-labeled trapping agent to the isotopically-labeled trapping agent is about 1:1.

4. The method of claim 1, wherein the drug metabolizing enzyme is a mixture of human liver microsomes.

5. The method of claim 1, wherein the drug metabolizing enzyme is cytochrome P450.

6. The method of claim 1, wherein the neutral loss mass spectrum is measured using ESI-MS/MS.

7. The method of claim 1, wherein the neutral loss mass spectrum is measured using FIA-MS/MS.

8. The method of claim 1, wherein the isotopic doublet differs by a mass of between 2 and 5 mass units.

9. The method of claim 8, wherein the isotopic doublet differs by a mass of 3 mass units.

10. The method of claim 1, wherein the isotopically-labeled trapping agent is labeled with at least one isotope selected from the group consisting of $^{13}C$, $^{15}N$ and $^{2}H$.

11. The method of claim 10, wherein the isotopically-labeled trapping agent is labeled with three isotopes selected from the group consisting of $^{13}C$ and $^{15}N$.

* * * * *